US008236352B2

(12) United States Patent
Bosch et al.

(10) Patent No.: US 8,236,352 B2
(45) Date of Patent: *Aug. 7, 2012

(54) GLIPIZIDE COMPOSITIONS

(75) Inventors: H. William Bosch, Bryn Mawr, PA (US); Niels P. Ryde, Malvern, PA (US); Rajeev A. Jain, Farmingham, MA (US); Jon Swanson, North Wales, PA (US); Robert Hontz, Newtown Square, PA (US); John G. Devane, Athlone (IE); Kenneth Ian Cumming, Essex (GB); Maurice Joseph Anthony Clancy, Celbridge (IE); Janet Elizabeth Codd, Wexford (IE); Gary G. Liversidge, Westchester, PA (US)

(73) Assignee: Alkermes Pharma Ireland Limited, Dublin (IE)

( * ) Notice: Subject to any disclaimer, the term of this patent is extended or adjusted under 35 U.S.C. 154(b) by 1113 days.

This patent is subject to a terminal disclaimer.

(21) Appl. No.: 10/701,064

(22) Filed: Nov. 5, 2003

(65) Prior Publication Data

US 2005/0019412 A1    Jan. 27, 2005

Related U.S. Application Data

(63) Continuation-in-part of application No. 09/337,675, filed on Jun. 22, 1999, which is a continuation-in-part of application No. 09/164,351, filed on Oct. 1, 1998, now abandoned, application No. 10/701,064, which is a continuation-in-part of application No. 10/276,400, filed as application No. PCT/US01/15983 on May 18, 2001, now abandoned.

(51) Int. Cl.
 *A61K 9/14* (2006.01)
 *A61K 9/20* (2006.01)
(52) U.S. Cl. .................... 424/489; 424/464; 424/465
(58) Field of Classification Search .................... None
 See application file for complete search history.

(56) References Cited

U.S. PATENT DOCUMENTS

| | | |
|---|---|---|
| 3,269,798 A | 8/1966 | Preston |
| 3,669,966 A | 6/1972 | Ambrogi et al. |
| 3,692,532 A | 9/1972 | Shankenberg et al. |
| 4,178,695 A | 12/1979 | Erbeia |
| 4,225,581 A | 9/1980 | Kreuter et al. |
| 4,389,397 A * | 6/1983 | Lo et al. .......................... 514/53 |
| 4,524,060 A | 6/1985 | Mughal et al. |
| 4,540,602 A | 9/1985 | Motoyama et al. |
| 4,562,069 A | 12/1985 | Hegasy et al. |
| 4,616,047 A | 10/1986 | Lafon |
| 4,642,903 A | 2/1987 | Davies |
| 4,657,901 A | 4/1987 | Ueda et al. |
| 4,665,081 A | 5/1987 | Doi et al. |
| 4,708,868 A | 11/1987 | Brickl et al. |
| 4,727,077 A | 2/1988 | Haga et al. |
| 4,757,059 A | 7/1988 | Sorenson |
| 4,765,990 A | 8/1988 | Sugimoto et al. |
| 4,783,484 A | 11/1988 | Violante et al. |
| 4,826,689 A | 5/1989 | Violanto et al. |
| 4,851,421 A | 7/1989 | Iwasaki et al. |
| 4,863,742 A | 9/1989 | Panoz et al. |
| 4,880,634 A | 11/1989 | Speiser |
| 4,904,668 A | 2/1990 | Kondo et al. |
| 4,917,816 A | 4/1990 | Self |
| 4,983,605 A | 1/1991 | Kondo et al. |
| 4,997,454 A | 3/1991 | Violante et al. |
| 5,002,952 A | 3/1991 | Kondo et al. |
| 5,024,843 A * | 6/1991 | Kuczynski et al. ...... 514/255.06 |
| 5,049,322 A | 9/1991 | Devissaguet et al. |
| 5,073,374 A | 12/1991 | McCarty |
| 5,098,907 A | 3/1992 | Kondo et al. |
| 5,110,605 A | 5/1992 | Acharya |
| 5,112,616 A | 5/1992 | McCarty |
| 5,118,528 A | 6/1992 | Fessi et al. |
| 5,133,908 A | 7/1992 | Stainmesse et al. |
| 5,145,684 A * | 9/1992 | Liversidge et al. ........... 424/489 |
| 5,156,767 A | 10/1992 | Fitzgerald et al. |
| 5,178,878 A | 1/1993 | Wehling et al. |
| 5,188,825 A | 2/1993 | Iles et al. |
| 5,215,758 A | 6/1993 | Krishnamurthy |
| 5,219,574 A | 6/1993 | Wehling et al. |
| 5,223,264 A | 6/1993 | Wehling et al. |
| 5,260,478 A | 11/1993 | Bacon et al. |
| 5,264,213 A | 11/1993 | Shibahara et al. |
| 5,264,610 A | 11/1993 | Bacon |
| 5,298,262 A | 3/1994 | Rajagopalan |
| 5,300,739 A | 4/1994 | Bittar |
| 5,302,401 A | 4/1994 | Liversidge et al. |
| 5,318,767 A | 6/1994 | Liversidge et al. |
| 5,326,552 A | 7/1994 | Na et al. |

(Continued)

FOREIGN PATENT DOCUMENTS

AU           699996 B      12/1998

(Continued)

OTHER PUBLICATIONS

Physcians' Desk Reference, 57th edition, pp. 2606-2607.
Wahlin-Boll et al., *Clin. Pharmacokinet.*, Jul.-Aug.: 363-72 (1982).
Lindahl et al.. "Characterization of Fluids from the Stomach and Proximal Jejunum in Men and Women", *Pharmaceutical Research*, vol. 14, No. 4, 1997, pp. 497-502.
Kondo et al., "Improved Oral Absorption of Enteric Coprecipitates of a Poorly Soluble Drug", *J. Pharm. Sciences*, 83(4): 566-570 (1994).
Kondo et al., "Improved Oral Absorption of a Poorly Water-Soluble Drug HO-221, by Wet-Bead Milling Particles in Submicron Region", *Chem. Pharm. Bull.*, 41(4): 737-740 (1993).
Kondo et al., "Pharmocokinetics of a Micronized, Poorly Water Soluble Drug, HO-221 in Experimental Animals", *Biol. Pharm. Bull.* 16(8): 796-800, (1993).
Guidance for Industry, Levothyroxine Sodium Tablets—In Vivo Pharmacokinetic and Bioavailability Studies and in Vitro Dissolution Testing, U.S. Department of Health and Human Services, Food and Drug Administration, Dec. 2000, pp. 1-8.
Journal of Microencapsulation, vol. 10, No. 1, pp. 89-99 (1993).
Labo-Pharma Probl. Tech., vol. 32, No. 348, pp. 835-837 (1984).
European Journal of Pharmaceutics and Biopharmaceutics, vol. 49, No. 3, pp. 237-242 (2000).
Pharmaceutical Research, vol. 16, No. 11, pp. 1722-1728 (1999).

(Continued)

*Primary Examiner* — Susan Tran
(74) *Attorney, Agent, or Firm* — Foley & Lardner LLP

(57) ABSTRACT

The present invention is directed to nanoparticulate compositions comprising glipizide. The glipizide particles of the composition preferably have an effective average particle size of less than about 2 microns.

49 Claims, 1 Drawing Sheet

U.S. PATENT DOCUMENTS

| | | | |
|---|---|---|---|
| 5,328,404 A | 7/1994 | Bacon | |
| 5,336,507 A | 8/1994 | Na et al. | |
| 5,338,761 A | 8/1994 | Nakajima et al. | |
| 5,340,564 A | 8/1994 | Illig et al. | |
| 5,346,702 A | 9/1994 | Na et al. | |
| 5,349,957 A | 9/1994 | Yudelson | |
| 5,352,459 A | 10/1994 | Hollister et al. | |
| 5,356,467 A | 10/1994 | Oshlack et al. | |
| 5,384,124 A | 1/1995 | Courteille et al. | |
| 5,399,363 A | 3/1995 | Liversidge et al. | |
| 5,401,492 A | 3/1995 | Kellar et al. | |
| 5,401,513 A | 3/1995 | Wehling et al. | |
| 5,429,824 A | 7/1995 | June | |
| 5,446,464 A | 8/1995 | Feldle | |
| 5,447,710 A | 9/1995 | Na et al. | |
| 5,451,393 A | 9/1995 | Liversidge et al. | |
| 5,464,632 A | 11/1995 | Cousin et al. | |
| 5,466,440 A | 11/1995 | Ruddy et al. | |
| 5,470,583 A | 11/1995 | Na et al. | |
| 5,472,683 A | 12/1995 | Illig | |
| 5,494,683 A | 2/1996 | Liversidge et al. | |
| 5,500,204 A | 3/1996 | Osifo | |
| 5,503,846 A | 4/1996 | Wehling et al. | |
| 5,510,118 A * | 4/1996 | Bosch et al. | 424/489 |
| 5,518,187 A | 5/1996 | Bruno et al. | |
| 5,518,738 A | 5/1996 | Eickhoff et al. | |
| 5,521,168 A | 5/1996 | Clark | |
| 5,521,218 A | 5/1996 | Osifo | |
| 5,525,328 A | 6/1996 | Bacon et al. | |
| 5,527,545 A | 6/1996 | Santus et al. | |
| 5,534,270 A | 7/1996 | De Castro | |
| 5,542,935 A | 8/1996 | Unger et al. | |
| 5,543,133 A | 8/1996 | Swanson et al. | |
| 5,552,160 A | 9/1996 | Liversidge et al. | |
| 5,560,931 A | 10/1996 | Eickhoff et al. | |
| 5,560,932 A | 10/1996 | Bagchi et al. | |
| 5,565,188 A | 10/1996 | Wong et al. | |
| 5,569,448 A | 10/1996 | Wong et al. | |
| 5,571,536 A | 11/1996 | Eickhoff et al. | |
| 5,573,749 A | 11/1996 | Illig | |
| 5,573,750 A | 11/1996 | Singh | |
| 5,573,783 A | 11/1996 | Desieno et al. | |
| 5,576,014 A | 11/1996 | Mizumoto et al. | |
| 5,580,579 A | 12/1996 | Ruddy et al. | |
| 5,585,108 A | 12/1996 | Ruddy et al. | |
| 5,587,143 A | 12/1996 | Wong | |
| 5,587,172 A | 12/1996 | Cherukuri et al. | |
| 5,587,180 A | 12/1996 | Allen, Jr. et al. | |
| 5,591,456 A | 1/1997 | Franson et al. | |
| 5,593,657 A | 1/1997 | Ruddy et al. | |
| 5,595,761 A | 1/1997 | Allen, Jr. et al. | |
| 5,595,762 A | 1/1997 | Derrieu et al. | |
| 5,607,697 A | 3/1997 | Alkire et al. | |
| 5,622,719 A | 4/1997 | Myers et al. | |
| 5,622,938 A | 4/1997 | Wong | |
| 5,628,981 A | 5/1997 | Liversidge et al. | |
| 5,631,023 A | 5/1997 | Kearney et al. | |
| 5,635,210 A | 6/1997 | Allen, Jr. et al. | |
| 5,639,475 A | 6/1997 | Bettman et al. | |
| 5,641,515 A | 6/1997 | Ramtoola | |
| 5,643,552 A | 7/1997 | Illig | |
| 5,656,299 A | 8/1997 | Kino et al. | |
| 5,662,883 A | 9/1997 | Bagchi et al. | |
| 5,665,331 A | 9/1997 | Bagchi et al. | |
| 5,709,886 A | 1/1998 | Bettman et al. | |
| 5,718,388 A | 2/1998 | Czekai et al. | |
| 5,718,919 A | 2/1998 | Ruddy et al. | |
| 5,741,522 A | 4/1998 | Violante et al. | |
| 5,747,001 A | 5/1998 | Wiedmann et al. | |
| 5,756,546 A | 5/1998 | Pirotte et al. | |
| 5,776,496 A | 7/1998 | Violante et al. | |
| 5,795,909 A | 8/1998 | Shashoua et al. | |
| 5,807,576 A | 9/1998 | Allen, Jr. et al. | |
| 5,807,577 A | 9/1998 | Ouali | |
| 5,807,578 A | 9/1998 | Acosta-Cuello et al. | |
| 5,811,388 A | 9/1998 | Friend et al. | |
| 5,811,404 A | 9/1998 | De Frees et al. | |
| 5,811,422 A | 9/1998 | Lam et al. | |
| 5,811,425 A | 9/1998 | Woods et al. | |
| 5,827,541 A | 10/1998 | Yarwood et al. | |
| 5,834,025 A | 11/1998 | De Garavilla et al. | |
| 5,851,553 A | 12/1998 | Myers et al. | |
| 5,853,756 A | 12/1998 | Mody et al. | |
| 5,862,999 A | 1/1999 | Czekai et al. | |
| 5,866,163 A | 2/1999 | Myers et al. | |
| 5,869,098 A | 2/1999 | Misra et al. | |
| 5,871,747 A | 2/1999 | Gengoux-Sedilik et al. | |
| 5,871,781 A | 2/1999 | Myers et al. | |
| 5,889,088 A | 3/1999 | Kisuno et al. | |
| 5,916,596 A * | 6/1999 | Desai et al. | 424/489 |
| 5,939,091 A * | 8/1999 | Eoga et al. | 424/441 |
| 5,972,389 A | 10/1999 | Shell et al. | |
| 6,001,928 A | 12/1999 | Harkness et al. | |
| 6,004,582 A | 12/1999 | Faour et al. | |
| 6,017,932 A | 1/2000 | Singh et al. | |
| 6,045,829 A | 4/2000 | Liversidge et al. | |
| 6,068,858 A | 5/2000 | Liversidge et al. | |
| 6,093,420 A | 7/2000 | Baichwal | |
| 6,117,455 A * | 9/2000 | Takada et al. | 424/501 |
| 6,153,225 A | 11/2000 | Lee et al. | |
| 6,165,506 A | 12/2000 | Jain et al. | |
| 6,177,103 B1 | 1/2001 | Pace et al. | |
| 6,177,104 B1 | 1/2001 | Allen et al. | |
| 6,193,960 B1 | 2/2001 | Metzger et al. | |
| 6,221,400 B1 | 4/2001 | Liversidge et al. | |
| 6,231,888 B1 | 5/2001 | Lerner et al. | |
| 6,264,922 B1 | 7/2001 | Wood et al. | |
| 6,267,989 B1 | 7/2001 | Liversidge et al. | |
| 6,270,806 B1 | 8/2001 | Liversidge et al. | |
| 6,316,029 B1 * | 11/2001 | Jain et al. | 424/484 |
| 6,368,620 B2 | 4/2002 | Liu et al. | |
| 6,375,986 B1 | 4/2002 | Ryde et al. | |
| 6,383,471 B1 * | 5/2002 | Chen et al. | 424/45 |
| 6,395,300 B1 | 5/2002 | Straub et al. | |
| 6,428,814 B1 | 8/2002 | Bosch | |
| 6,431,478 B1 | 8/2002 | Reed et al. | |
| 6,432,381 B2 | 8/2002 | Liversidge et al. | |
| 6,458,373 B1 | 10/2002 | Lambert et al. | |
| 6,458,777 B1 | 10/2002 | Sonis et al. | |
| 6,464,988 B1 | 10/2002 | Gidwani et al. | |
| 6,555,139 B2 | 4/2003 | Sharma | |
| 6,579,352 B1 | 6/2003 | Tanaka et al. | |
| 6,579,895 B2 | 6/2003 | Karim et al. | |
| 6,583,180 B2 | 6/2003 | Link et al. | |
| 6,592,903 B2 | 7/2003 | Ryde et al. | |
| 6,604,698 B2 | 8/2003 | Verhoff et al. | |
| 7,198,795 B2 | 4/2007 | Cooper et al. | |
| 2002/0002294 A1 | 1/2002 | Cushman et al. | |
| 2002/0012675 A1 * | 1/2002 | Jain et al. | 424/400 |
| 2002/0055462 A1 | 5/2002 | Reed et al. | |
| 2002/0165265 A1 | 11/2002 | Hunter et al. | |
| 2003/0077329 A1 | 4/2003 | Kipp et al. | |
| 2004/0033267 A1 | 2/2004 | Merisko-Liversidge et al. | |
| 2004/0198644 A1 | 10/2004 | Bender et al. | |
| 2007/0048378 A1 | 3/2007 | Swanson et al. | |
| 2007/0160675 A1 | 7/2007 | Devane et al. | |

FOREIGN PATENT DOCUMENTS

| | | |
|---|---|---|
| CA | 2346001 | 4/2000 |
| EP | 0 220 760 A2 | 10/1985 |
| EP | 0 220 143 | 4/1987 |
| EP | 0 262 560 A2 | 9/1987 |
| EP | 0 375 662 | 6/1990 |
| EP | 0 486 153 A2 | 5/1992 |
| EP | 0 499 299 | 8/1992 |
| EP | 0 600 532 A2 | 6/1994 |
| EP | 0 602 702 A1 | 6/1994 |
| EP | 0 636 365 A1 | 2/1995 |
| EP | 0 601 619 | 12/1996 |
| EP | 0 577 215 | 3/2000 |
| EP | 1 010 435 A1 | 6/2000 |
| EP | 1 800 666 A1 | 6/2007 |
| FR | 2304326 | 10/1976 |
| GB | 1 166 651 A | 5/1986 |
| GB | 2316316 A * | 2/1998 |
| JP | 48-043848 | 11/1970 |
| JP | 57-26615 | 2/1982 |

| | | |
|---|---|---|
| JP | 61-218516 | 9/1986 |
| JP | 62-126127 | 6/1987 |
| JP | 63-005021 | 1/1988 |
| JP | 63-240936 | 10/1988 |
| JP | 2-167222 | 6/1990 |
| JP | 03/066613 | 3/1991 |
| JP | 4-502318 | 4/1992 |
| JP | 4-295420 | 10/1992 |
| JP | 6-227967 | 8/1994 |
| JP | 07-112936 | 5/1995 |
| JP | 8-151322 | 6/1996 |
| JP | 8-507075 | 7/1996 |
| JP | 8-259460 | 10/1996 |
| JP | 9-241178 | 9/1997 |
| JP | 09-271658 | 10/1997 |
| JP | 2004-513886 | 5/2004 |
| WO | WO 90/15593 | 12/1990 |
| WO | WO 91/13612 | 9/1991 |
| WO | WO 93/10760 | 6/1993 |
| WO | WO 93-10760 | 6/1993 |
| WO | WO 93/10767 | 6/1993 |
| WO | WO 93/13773 | 7/1993 |
| WO | WO 93/25190 | 12/1993 |
| WO | WO 93/25190 A1 | 12/1993 |
| WO | WO 93/25194 | 12/1993 |
| WO | WO 93/25195 | 12/1993 |
| WO | WO 94/18954 | 9/1994 |
| WO | WO 94/20072 | 9/1994 |
| WO | WO 95/05164 | 2/1995 |
| WO | WO 95/22318 A1 | 8/1995 |
| WO | WO 95/27475 | 10/1995 |
| WO | WO 96/03132 | 2/1996 |
| WO | WO 96/13251 A1 | 5/1996 |
| WO | WO 96/20698 | 7/1996 |
| WO | WO 96/20698 A2 | 7/1996 |
| WO | WO 96/24336 A1 | 8/1996 |
| WO | WO 96/24339 A1 | 8/1996 |
| WO | WO 96/25918 | 8/1996 |
| WO | WO 96/84335 | 8/1996 |
| WO | WO 97/18796 | 5/1997 |
| WO | WO 98/04291 | 2/1998 |
| WO | WO 98/07414 | 2/1998 |
| WO | WO 9807414 A1 * | 2/1998 |
| WO | WO 98/14174 | 4/1998 |
| WO | WO 98/29098 | 7/1998 |
| WO | WO 98/31360 | 7/1998 |
| WO | WO 9831360 A1 * | 7/1998 |
| WO | WO 98/35666 | 8/1998 |
| WO | WO 98/46215 A1 | 10/1998 |
| WO | WO 99/02665 | 1/1999 |
| WO | WO 99/25354 | 5/1999 |
| WO | WO 99/38493 | 8/1999 |
| WO | WO 99/65469 | 12/1999 |
| WO | WO 00/13672 | 3/2000 |
| WO | WO 00/18374 | 4/2000 |
| WO | WO 00/32189 | 6/2000 |
| WO | WO 00/47196 | 8/2000 |
| WO | WO 00/51572 | 9/2000 |
| WO | WO 0053164 | 9/2000 |
| WO | WO 01/17546 A1 | 3/2001 |
| WO | WO 01/26635 | 4/2001 |
| WO | WO 01/45674 A1 | 6/2001 |
| WO | WO 01/78505 A1 | 10/2001 |
| WO | WO 01/78680 A2 | 10/2001 |
| WO | WO 01/91750 A1 | 12/2001 |
| WO | WO 01/92584 A1 | 12/2001 |
| WO | WO 02/24163 | 3/2002 |
| WO | WO 02/067901 A1 | 9/2002 |
| WO | WO 02/098565 | 12/2002 |
| WO | WO 03/080027 A1 | 10/2003 |
| WO | WO 03/094894 A1 | 11/2003 |
| WO | WO 03/103633 A1 | 12/2003 |

OTHER PUBLICATIONS

S.T.P. Pharma Sciences, vol. 2, No. 2, pp. 186-192 (1992).
Office Action dated Sep. 22, 2008 for related U.S. Appl. No. 11/980,586, 14 pgs.
Office Action dated Sep. 18, 2008 for related U.S. Appl. No. 11/979,231, 7 pgs.
Office Action dated Oct. 16, 2008 for related U.S. Appl. No. 11/898,274, 8 pgs.
Office Action dated Nov. 12, 2008 for related U.S. Appl. No. 10/667,470, 20 pages.
Translation of Notice of Rejection for related Japanese Patent Application No. 2002-528199, 3 pgs., dated Oct. 30, 2008.
Notice of Rejections for Japanese Patent Application No. 2001-529425, dated Jan. 6, 2009, 5 pgs.
Calvo et al., "Development of Positively Charged Colloidal Drug Carriers: Chitosan-Coated Polyester nanocapsules and Submicron-Emulsions," Colloid. Polym. Sci., 275, pp. 46-53 (1997).
Rock et al., "Control of Calcium Carbonate Particle Size and Shape by Precipitation from CTAB/Alcohol/Hexadecane Mixtures," Colloid. Polym. Sci., 275, pp. 893-896 (1997).
Notice of Rejections for Japanese Patent Application No. 2001-583733, dated Jan. 6, 2009., 5 pgs.
Office Action for related U.S. Appl. No. 10/697,716 dated Apr. 15, 2009.
Office Action for related U.S. Appl. No. 10/677,857 dated Jan. 21, 2009.
Office Action for related U.S. Appl. No. 11/650,412, dated May 12, 2009.
Office Action for related U.S. Appl. No. 10/697,703, dated Dec. 9, 2008.
Office Action for related U.S. Appl. No. 10/667,470, dated May 19, 2009.
Office Action for related U.S. Appl. No. 11/979,231, dated Mar. 13, 2009.
Office Action cited in related U.S. Appl. No. 11/898,274 dated May 5, 2009.
Office Action cited in related U.S. Appl. No. 10/677,857 dated Jul. 8, 2009.
Office Action cited in related U.S. Appl. No. 10/697,703 dated Jul. 9, 2009.
Office Action cited in related U.S. Appl. No. 10/667,470 dated May 19, 2009.
Notice of Rejections completed Aug. 26, 2009 for related Japanese Patent Application No. 2001-583733.
Office Action cited in related U.S. Appl. No. 10/619,539 dated Sep. 8, 2009.
Office Action cited in related U.S. Appl. No. 11/979,231 dated Sep. 16, 2009.
Office Action cited in related U.S. Appl. No. 10/697,716 dated Sep. 15, 2009.
Office Action cited in related U.S. Appl. No. 11/980,720 dated Oct. 5, 2009.
Office Action cited in related U.S. Appl. No. 11/980,720, dated Dec. 22, 2010.
European Search Report cited in related EP Patent Application No. EP 10 01 0944, dated Dec. 13, 2010.
Office Action cited in related U.S. Appl. No. 11/898,274, dated Oct. 23, 2009.
Office Action cited in related U.S. Appl. No. 10/667,470, dated Dec. 29, 2009.
Office Action cited in related U.S. Appl. No. 11/979,240, dated Dec. 16, 2009.
Notice of Reasons for Rejection cited in related Japanese Patent Application No. 2004-510760 dated Dec. 2, 2009, 4 pgs.
Notice of Reasons for Rejection cited in related Japanese Patent Application No. 2004-521891 dated Dec. 22, 2009, 3 pgs.
Notice of Reasons for Rejection cited in related Japanese Patent Application No. 2003-565446, dated Jan. 20, 2010, 4 pgs.
Office Action cited in related U.S. Appl. No. 11/979,231, dated Mar. 16, 2010.
Office Action cited in related U.S. Appl. No. 11/980,720, dated Mar. 29, 2010.
Butler et al., "Effects of Protein Stabilizing Agents on Thermal Backbone Motions: A Disulfide Trapping Study," Biochemistry, vol. 35, pp. 10595-10600 (1996).
Canadian Office Action for related Canadian Patent Application No. 2,488,499, dated Feb. 8, 2010.
Office Action cited in related U.S. Appl. No. 10/697,703, dated Feb. 18, 2010.

Office Action cited in related U.S. Appl. No. 09/337,675, dated Feb. 18, 2010.
Office Action cited in related U.S. Appl. No. 12/292,395, dated May 26, 2010.
Damascelli et al., Intraarterial Chemotherapy with Polyoxyethylated Castor Oil Free Paclitaxel, Incorporated in Albumin Nanoparticles (ABI-007) Phase I Study of Patients with Squamous Cell Carcinoma of the Head and Neck and Anal Canal: Preliminary Evidence of Clinical Activity; 2001 Cancer, vol. 92, No. 10, pp. 2592-2602.
Office Action cited in related U.S. Appl. No. 11/928,278, dated Dec. 28, 2009.
Office Action cited in related U.S. Appl. No. 11/928,250, dated Dec. 29, 2009.
Office Action cited in related U.S. Appl. No. 11/928,289, dated Dec. 30, 2009.
Notice of Reasons for Rejections cited in related Japanese Patent Application No. 2003-577857, dated Mar. 29, 2010.
Office Action cited in related U.S. Appl. No. 11/928,250, dated Aug. 4, 2010.
Office Action cited in related U.S. Appl. No. 11/928,278, dated Aug. 4, 2010.
Office Action cited in related U.S. Appl. No. 11/928,289, dated Aug. 3, 2010.
Office Action cited in related U.S. Appl. No. 10/667,470, dated Jul. 27, 2010.
Office Action cited in related U.S. Appl. No. 09/337,675, dated Aug. 30, 2010.
Josefsson et al., "Suppression of Type II Collagen-Induced Arthritis by the Endogenous Estrogen Metabolite 2-Methoxyestradiol," *Arthritis & Rheumatism*, vol. 40, Issue 1, pp. 154-163 (1997).
Office Action cited in related U.S. Appl. No. 12/870,722, dated Oct. 7, 2010.
Office Action cited in related U.S. Appl. No. 12/870,745, dated Oct. 7, 2010.
Office Action cited in related U.S. Appl. No. 12/076,247, dated Aug. 5, 2010.
Office Action cited in related U.S. Appl. No. 12/320,431, dated Sep. 30, 2010.
Merriam-Webster's Collegiate Dictionary, 10$^{th}$ edition, Merriam-Webster Incorp.: Springfield, MA, 1993, pp. 311.
International Search Report for related International Patent Application No. PCT/US2009/036965, completed Jun. 19, 2009.
Written Opinion of the International Searching Authority for related International Patent Application No. PCT/US2009/036965, completed Jun. 19, 2009.
Notice of Rejections for related Japanese Patent Application No. 2003-577857 completed Jul. 6, 2009, 3 pgs.
Notice of Decision to Grant dated Aug. 30, 2010 cited in related Japanese Patent Application No. 2003-565446.
Canadian Office Action dated Mar. 10, 2010, cited in related Canadian Patent Application No. 2,479,665.
European Search Report for related EP Patent Application No. 10179894, dated Nov. 4, 2010.
Office Action cited in related U.S. Appl. No. 10/697,703, dated Nov. 9, 2010.
Office Action cited in related U.S. Appl. No. 11/367,716, dated Nov. 10, 2010.
Office Action cited in related U.S. Appl. No. 12/117,982, dated Dec. 1, 2010.
Office Action cited in related U.S. Appl. No. 12/292,395, dated Dec. 6, 2010.
Office Action cited in related U.S. Appl. No. 09/337,675, dated Jan. 11, 2011.
Canadian Office Action cited in related Canadian Patent Application No. 2475092, dated Jan. 11, 2011.
Calvo et al., "Effect of lysozyme on the stability of polyester nanocapsules and nanoparticles: stabilization approaches," *Biomaterials*, vol. 18, No. 19, pp. 1305-1310 (1997).
Tian et al., Structural Stability Effects on Adsorption of Bacteriophage T4 Lysozyme to Colloidal Silica, *J. Colloid. Interface Sci.*, vol. 200, pp. 146-154 (1998).

Office Action cited in related U.S. Appl. No. 12/117,982, dated Feb. 2, 2011.
Canadian Office Action cited in related Canadian Patent Application No. 2488499, dated Dec. 16, 2010.
Office Action cited in related U.S. Appl. No. 11/367,716, dated May 19, 2011.
Office Action cited in related U.S. Appl. No. 11/980,720, dated May 26, 2011.
Office Action cited in related U.S. Appl. No. 10/677,857, dated Jun. 7, 2011.
Office Action cited in related U.S. Appl. No. 12/483,188, dated Jun. 23, 2011.
Office Action cited in related U.S. Appl. No. 12/117,982, dated Jul. 8, 2011.
Office Action cited in related U.S.Appl. No. 12/068,706, dated Jul. 20, 2011.
Office Action cited in related U.S. Appl. No. 09/337,675, dated Aug. 1, 2011.
Office Action cited in related U.S. Appl. No. 10/619,539, dated Mar. 15, 2011.
Office Action cited in related U.S. Appl. No. 12/870,722, dated Mar. 29, 2011.
Office Action cited in related U.S. Appl. No. 12/870,745, dated Apr. 1, 2011.
Office Action cited in related U.S. Appl. No. 12/076,247, dated Apr. 14, 2011.
Purohit et al., Inhibition of Tumor Necrosis Factor a-Stimulated Aromatase Activity by Microtubule-Stabilizing Agents, Paclitaxel and 2-Methoxyestradiol, *Biochemical and Biophysical Research Communications*, vol. 261, Issue 1, Jul. 22, 1999, pp. 214-217.
Arsenault et al., Taxol Involution of Collagen-Indued Arthritis: Ultrastructural Correlation with the Inhibition of Synovitis and Neovascularization Clinical Immunology and Immunopathology, vol. 86, Issue 3, Mar. 1998, pp. 280-289.
Office Action cited in related U.S. Appl. No. 12/320,431, dated Apr. 15, 2011.
Office Action cited in related U.S. Appl. No. 11/928,250, dated Apr. 25, 2011.
Office Action cited in related U.S. Appl. No. 11/928,278, dated Apr. 27, 2011.
Office Action cited in related U.S. Appl. No. 12/928,289, dated Apr. 27, 2011.
Office Action cited in related U.S. Appl. No. 10/667,470, dated May 9, 2011.
Office Action cited in related U.S. Appl. No. 12/292,091, dated Jan. 18, 2012.
Czeslik et al., "Effect of Temperature on the Conformation of Lysozyme Adsorbed to Silica Particles," *Phys. Chem. Chem. Phys.*, vol. 3, pp. 235-239 (2001).
Abraham, "LXXVII. Some Properties of Egg-White Lysozyme," pp. 622-630 (1939).
Office Action cited in related U.S. Appl. No. 09/337,675, dated Feb. 7, 2012.
Written Opinion cited in related Singapore Patent Appln. No. 201006315-4, dated Dec. 2, 2011.
Office Action cited in related U.S. Appl. No. 12/729,018, dated Feb. 23, 2012.
Office Action cited in related U.S. Appl. No. 12/729,018, dated Oct. 14, 2011.
Notice of Reasons for Rejection cited in related Japanese Patent Application No. 2008-227248, dated Oct. 31, 2011.
Canadian Office Action cited in related Canadian Patent Application No. 2,488,499, dated Oct. 17, 2011.
Decision on Rejection cited in related Japanese Patent Application No. 2001-583733, dated Jun. 9, 2010, 3 pgs.
"Design and Evaluation of Oral Administration Drug Formulation", *Pharmaceutical Industry Time Signal Company*, pp. 167-168 (1995).

\* cited by examiner

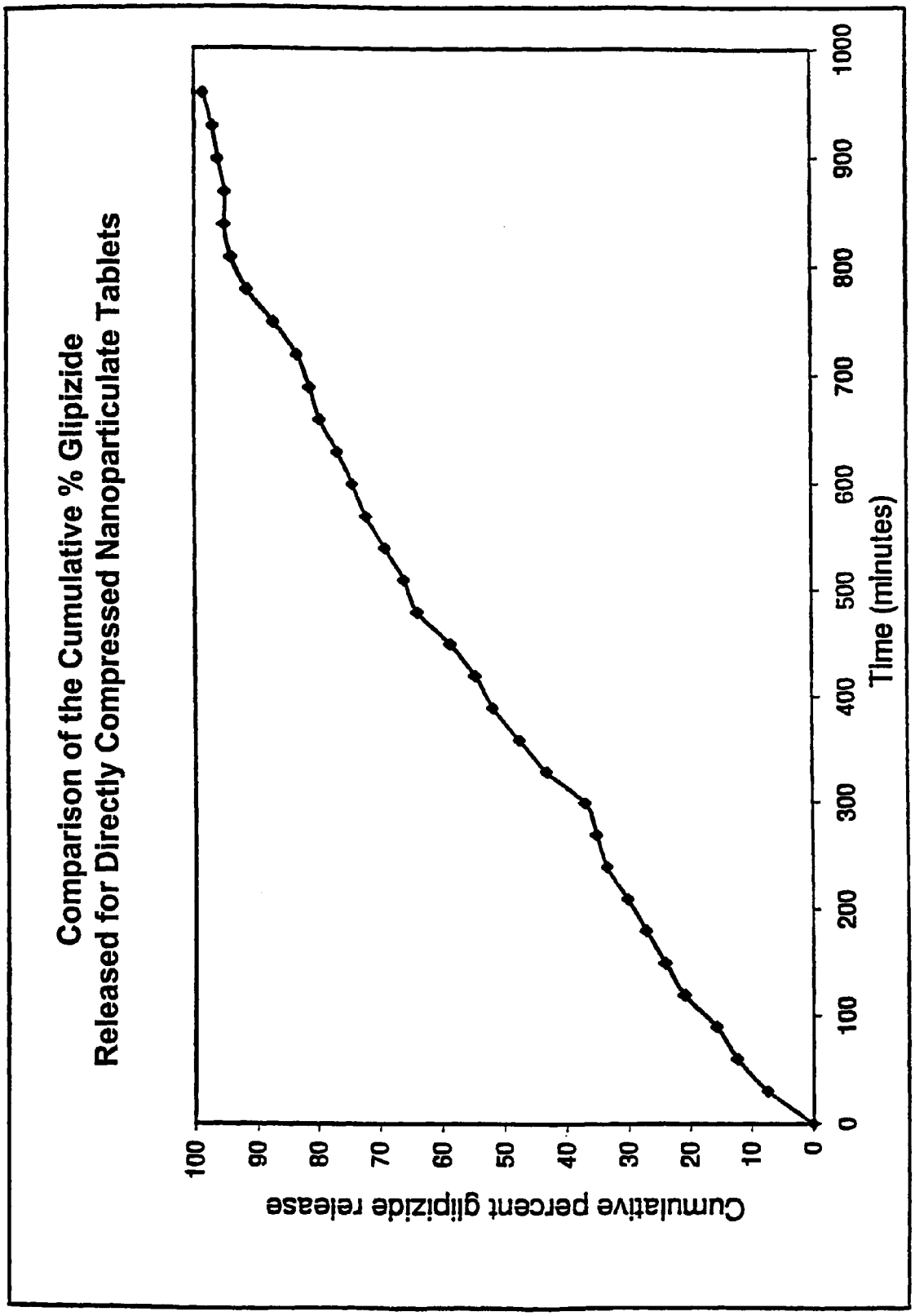

US 8,236,352 B2

GLIPIZIDE COMPOSITIONS

RELATED APPLICATIONS

This application is a continuation-in-part of U.S. patent application Ser. No. 09/337,675, filed on Jun. 22, 1999, which is continuation-in-part of U.S. patent application Ser. No. 09/164,351, filed on Oct. 1, 1998. The present application is also a continuation-in-part of U.S. patent application Ser. No. 10/276,400, filed on Jan. 15, 2003, which is a national stage application of PCT/US01/15983, filed on May 18, 2001, which claims priority of U.S. patent application Ser. No. 09/572,961, filed on May 18, 2000, now U.S. Pat. No. 6,316,029.

FIELD OF THE INVENTION

The present invention relates to novel compositions of glipizide, comprising glipizide particles having an effective average particle size of less than about 2000 nm and at least one surface stabilizer that is preferably adsorbed to or associated with the surface of the glipizide particles.

BACKGROUND OF THE INVENTION

A. Background Regarding Nanoparticulate Active Agent Compositions

Nanoparticulate active agent compositions, first described in U.S. Pat. No. 5,145,684 ("the '684 patent"), are particles consisting of a poorly soluble therapeutic or diagnostic agent having associated with the surface thereof a non-crosslinked surface stabilizer. The '684 patent does not describe nanoparticulate glipizide compositions.

Methods of making nanoparticulate active agent compositions are described, for example, in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles." These patents do not describe methods of making nanoparticulate glipizide.

Nanoparticulate active agent compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for "Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Non-ionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly(ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(−)Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate," U.S. Pat. No. 6,428,814 for "Bioadhesive nanoparticulate compositions having cationic surface stabilizers;" U.S. Pat. No. 6,431,478 for "Small Scale Mill;" U.S. Pat. No. 6,432,381 for "Methods for Targeting Drug Delivery to the Upper and/or Lower Gastrointestinal Tract," and U.S. Pat. No. 6,592,903 for "Nanoparticulate Dispersions Comprising a Synergistic Combination of a Polymeric Surface Stabilizer and Dioctyl Sodium Sulfosuccinate," all of which are specifically incorporated by reference. In addition, U.S. Patent Application No. 20020012675 A1, published on Jan. 31, 2002, for "Controlled Release Nanoparticulate Compositions," and WO 02/098565 for "System and Method for Milling Materials," describe nanoparticulate active agent compositions, and are specifically incorporated by reference. None of these references describe nanoparticulate glipizide compositions.

Amorphous small particle compositions are described, for example, in U.S. Pat. No. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;" U.S. Pat. No. 5,741,522 for "Ultrasmall, Non-aggregated Porous Particles of Uniform Size for Entrapping Gas Bubbles Within and Methods;" and U.S. Pat. No. 5,776,496, for "Ultrasmall Porous Particles for Enhancing Ultrasound Back Scatter." These references do not describe nanoparticulate glipizide.

B. Background Regarding Glipizide

Glipizide is a sulfonylurea antidiabetic drug, first described in U.S. Pat. No. 3,669,966 issued on Jun. 13, 1972, to Carlos Erba S.P.A. The '966 patent claims are directed to chemical compounds and processes for preparing the sulfonyl urea drugs.

Glipizide is used to treat type 2 (noninsulin-dependent) diabetes (formerly known as "adult-onset" diabetes), particularly in people whose diabetes cannot be controlled by diet alone. Glipizide lowers blood sugar by stimulating the pancreas to secrete insulin and helping the body use insulin efficiently. The pancreas must be capable of producing insulin for this medication to work. The drug is marketed under the trade names Glucotrol (Pfizer, Inc.).

Glipizide is a crystalline solid that melts at 208-209° C. when crystallized from ethanol. The compound has the chemical name 1-cyclohexyl-3-[[p-[2-(5-methylpyrazinecarboxamido)ethyl]-phenyl]sulfonyl]urea, the chemical formula $C_{21}H_{27}N_5O_4S$, and the following chemical structure:

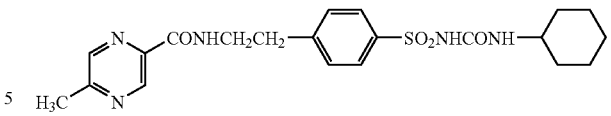

Peak plasma concentrations of conventional glipizide occur 1-3 hours after a single oral dose. *Physicians' Desk Reference*, 57th Edition, p. 2606-7. Total absorption of an oral dose is unaffected by food, but absorption is delayed by about 40 minutes. Thus, conventional forms of glipizide are more effective when administered about 30 minutes before a meal in diabetic subjects. Id.

Glipizide is indicated as an adjunct to diet for the control of hyperglycemia and its associated symptomatology in subjects with non-insulin dependent diabetes mellitus (NIDDM; type II). *Physicians' Desk Reference*, 57th Edition, p. 2606-7.

The administration of oral hypoglycemic drugs has been shown to be associated with increased cardiovascular mortality as compared to treatment with diet alone or diet plus insulin. In addition, all sulfonylurea drugs are capable of producing severe hypoglycemia. Other potential adverse effects of glipizide include gastrointestinal disturbances, allergic skin reactions, leukopenia, agranolucytosis, thrombocytopenia, hemolytic anemia, aplastic anemia, pancytopenia, hepatic porphyria, and disulfiram-like reactions, and hyponatremia. *Physicians' Desk Reference*, 57th Edition, p. 2606-7.

U.S. Pat. No. 4,708,868 to Brickl et al., issued on Nov. 24, 1987, is directed to a method of preparing an oral antidiabetic pharmaceutical composition containing an antidiabetic sulfonyl urea as the active ingredient. The process comprises dissolving or emulsifying in an inert solvent in the presence of at least one solubilizing or emulsifying substance: (a) an acid antidiabetic sulfonyl urea with a basic excipient, or (b) an amphoteric antidiabetic sulfonyl urea with a basic or acid excipient, or (c) a basic antidiabetic sulfonyl urea with an acid excipient. Next, the resulting solution or emulsion is applied to the surface of a water-insoluble carrier, followed by drying the thus treated waster-insoluble carrier. Brickl et al. also claims the composition prepared by the recited process. Brickl et al. do not describe micron size or nanometer sized particles.

U.S. Pat. No. 6,464,988 to Gidwani et al., issued on Oct. 15, 2002, claims an inclusion complex of glipizide and a nonionic surfactant with a cyclodextrin or a cyclodextrin derivative, in combination with at least one pharmaceutically acceptable excipient. The glipizide is in micronized particle sizes of 1.0 to 40 µm and the cyclodextrin or cyclodextrin derivative is in particle sizes of 10 to 250 µm.

U.S. Pat. No. 6,555,139 to Sharma, issued on Apr. 29, 2003, claims a process for preparing a pharmaceutically active material having an average particle size of from about 1.0 to 15.0 micrometers. The process comprises microfludizing a composition comprising particles of a water-insoluble pharmaceutical material in an aqueous carrier liquid in the presence of at least 0.01% weight cyclodextrin particles.

U.S. Pat. No. 6,583,180 to Link et al., issued on Jun. 24, 2003, claims a method of treating a disease by administering a novel compound of Formula I as shown in the patent and an antidiabetic drug which can be glipizide.

U.S. Pat. No. 6,604,698 to Verhoff et al., issued on Aug. 12, 2003, claims a process for preparing a dispersion of solid particles of a milled substrate in a fluid carrier comprising the use of a combination of large and small milling media in a milling device.

None of the prior art patent references teach or suggest a nanoparticulate glipizide composition according to the present invention.

Glipizide has been used as an antidiabetic drug for several years, but absorption of the drug from tablets has been shown to be retarded due to delayed tablet disintegration and drug dissolution. See Wahlin-Boll et al., *Clin. Pharmacokinet.*, July-August: 363-72 (1982). Thus, there is a need for glipizide in a form which achieves facile absorption.

There is a need in the art for glipizide compositions which can decrease frequency of dosing, improve bioavailability, improve clinical efficacy, and potentially reduce side effects. The present invention satisfies these needs.

SUMMARY OF THE INVENTION

The present invention relates to nanoparticulate glipizide compositions. The compositions comprise glipizide and at least one surface stabilizer preferably adsorbed on or associated with the surface of the glipizide particles. The nanoparticulate glipizide particles have an effective average particle size of less than about 2 microns.

Another aspect of the invention is directed to pharmaceutical compositions comprising a nanoparticulate glipizide composition of the invention. The pharmaceutical compositions preferably comprise glipizide, at least one surface stabilizer, and at least one pharmaceutically acceptable carrier, as well as any desired excipients. Advantages and properties of the compositions of the invention are described herein.

The invention further discloses a method of making a nanoparticulate glipizide composition. Such a method comprises contacting glipizide and at least one surface stabilizer for a time and under conditions sufficient to provide a nanoparticulate glipizide composition. The one or more surface stabilizers can be contacted with glipizide either before, preferably during, or after size reduction of the glipizide.

The present invention is also directed to methods of treatment using the nanoparticulate glipizide compositions of the invention for treatment of disorders where a blood-glucose lowering drug is indicated. Such disorders include but are not limited to non-insulin dependent diabetes mellitus.

Both the foregoing general description and the following detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE FIGURES

FIG. 1—Shows the controlled release of nanoparticulate glipizide from directly compressed Methocel® tablets.

DETAILED DESCRIPTION OF THE INVENTION

The present invention is directed to nanoparticulate glipizide compositions. The compositions comprise glipizide and at least one surface stabilizer that is preferably adsorbed on or associated with the surface of the drug. The nanoparticulate glipizide particles have an effective average particle size of less than about 2 microns.

As taught in the '684 patent, not every combination of surface stabilizer and active agent will result in a stable nanoparticulate composition. It was surprisingly discovered that stable nanoparticulate glipizide formulations can be made.

The current formulations of glipizide suffer from the following problems: (1) the poor solubility of the drug results in a relatively low bioavailability; (2) dosing must be repeated several times each day; and (3) a wide variety of side effects are associated with the current dosage forms of the drug.

The present invention overcomes problems encountered with the prior art glipizide formulations. Specifically, the nanoparticulate glipizide formulations of the invention may offer the following advantages: (1) faster onset of action; (2) a potential decrease in the frequency of dosing; (3) smaller doses of glipizide required to obtain the same pharmacological effect; (4) increased bioavailability; (5) an increased rate of dissolution; (6) improved performance characteristics for oral, intravenous, subcutaneous, or intramuscular injection, such as higher dose loading and smaller tablet or liquid dose volumes; (7) improved pharmacokinetic profiles, such as improved $T_{max}$, $C_{max}$, and AUC profiles; (8) substantially similar or bioequivalent pharmacokinetic profiles of the nanoparticulate glipizide compositions when administered in the fed versus the fasted state; (9) bioadhesive glipizide formulations, which can coat the gut or the desired site of application and be retained for a period of time, thereby increasing the efficacy of the drug as well as eliminating or decreasing the frequency of dosing; (10) high redispersibility of the nanoparticulate glipizide particles present in the compositions of the invention following administration; (11) the nanoparticulate glipizide compositions can be formulated in a dried form which readily redisperses; (12) low viscosity liquid nanoparticulate glipizide dosage forms can be made; (13) for liquid nanoparticulate glipizide compositions having a low viscosity—better subject compliance due to the perception of a lighter formulation which is easier to consume and digest; (14) for liquid nanoparticulate glipizide compositions having a low viscosity—ease of dispensing because one can use a cup or a syringe; (15) the nanoparticulate glipizide compositions can be used in conjunction with other active agents; (16) the nanoparticulate glipizide compositions can be sterile filtered; (17) the nanoparticulate glipizide compositions are suitable for parenteral administration; and (18) the nanoparticulate glipizide compositions do not require organic solvents or pH extremes.

A preferred dosage form of the invention is a solid dosage form, although any pharmaceutically acceptable dosage form can be utilized. Exemplary solid dosage forms include, but are not limited to, tablets, capsules, sachets, lozenges, powders, pills, or granules. The solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof. A solid dose tablet formulation is preferred.

The present invention is described herein using several definitions, as set forth below and throughout the application.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

"Conventional" or "non-nanoparticulate active agent" shall mean an active agent which is solubilized or which has an effective average particle size of greater than about 2 microns. Nanoparticulate active agents as defined herein have an effective average particle size of less than about 2 microns.

"Pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salts" as used herein refers to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Poorly water soluble drugs" as used herein means those having a solubility of less than about 30 mg/ml, preferably less than about 20 mg/ml, preferably less than about 10 mg/ml, or preferably less than about 1 mg/ml. Such drugs tend to be eliminated from the gastrointestinal tract before being absorbed into the circulation.

As used herein with reference to stable drug particles, "stable" includes, but is not limited to, one or more of the following parameters: (1) that the glipizide particles do not appreciably flocculate or agglomerate due to interparticle attractive forces, or otherwise significantly increase in particle size over time; (2) that the physical structure of the glipizide particles is not altered over time, such as by conversion from an amorphous phase to crystalline phase; (3) that the glipizide particles are chemically stable; and/or (4) where the glipizide has not been subject to a heating step at or above the melting point of the glipizide in the preparation of the nanoparticles of the invention.

"Therapeutically effective amount" as used herein with respect to a drug dosage, shall mean that dosage that provides the specific pharmacological response for which the drug is administered in a significant number of subjects in need of such treatment. It is emphasized that "therapeutically effective amount," administered to a particular subject in a particular instance will not always be effective in treating the diseases described herein, even though such dosage is deemed a "therapeutically effective amount" by those skilled in the art. It is to be further understood that drug dosages are, in particular instances, measured as oral dosages, or with reference to drug levels as measured in blood.

I. Preferred Characteristics of the Nanoparticulate Glipizide Compositions of the Invention A. Increased Bioavailability, Frequency of Dosing, and Dosage Quantity The nanoparticulate glipizide compositions of the invention may preferably exhibit increased bioavailability and require smaller doses as compared to prior non-nanoparticulate glipizide compositions administered at the same dose.

Any drug, including glipizide, can have adverse side effects. Thus, lower doses of glipizide that can achieve the same or better therapeutic effects as those observed with larger doses of non-nanoparticulate glipizide compositions are desired. Such lower doses may be realized with the nanoparticulate glipizide compositions of the invention because the nanoparticulate glipizide compositions may exhibit greater bioavailability as compared to non-nanoparticulate glipizide formulations, which means that smaller dose of glipizide are likely required to obtain the desired therapeutic effect.

The recommended starting total daily dose of glipizde is 5 milligrams taken before breakfast, with geriatric patients or those suffering from liver disease started at 2.5 mg/day. Depending upon blood glucose response, the initial dose may be increased in increments of 2.5 to 5 milligrams. The maximum recommended daily dose is 40 milligrams; total daily dosages above 15 milligrams are usually divided into 2 equal doses that are taken before meals.

In contrast, the glipizide compositions of the invention may be administered less frequently and at lower doses in dosage forms such as liquid dispersions, powders, sprays, solid redispersable dosage forms, ointments, creams, etc. Exemplary types of formulations useful in the present invention include, but are not limited to, liquid dispersions, gels, aerosols (pulmonary and nasal), ointments, creams, solid dose forms, etc. of nanoparticulate glipizide. Lower dosages can be used because the small particle size of the glipizide particles ensure greater absorption, and in the case of bioadhesive nanoparticulate glipizide compositions, the glipizide is retained at the desired site of application for a longer period of time as compared to conventional glipizide dosage forms.

In one embodiment of the invention, the therapeutically effective amount of the nanoparticulate glipizide compositions is $\frac{1}{6}$, $\frac{1}{5}$, $\frac{1}{4}$, $\frac{1}{3}^{rd}$, or $\frac{1}{2}$ of the therapeutically effective amount of a non-nanoparticulate glipizide composition.

Such lower doses are preferred as they may decrease or eliminate adverse effects of the drug. In addition, such lower doses decrease the cost of the dosage form and may increase patient compliance.

B. Pharmacokinetic Profiles of the Nanoparticulate Glipizide Compositions of the Invention The invention also preferably provides glipizide compositions having a desirable pharmacokinetic profile when administered to mammalian subjects. The desirable pharmacokinetic profile of the glipizide compositions preferably includes, but is not limited to: (1) a $T_{max}$ for glipizide, when assayed in the plasma of a mammalian subject following administration, that is preferably less than the $T_{max}$ for a non-nanoparticulate glipizide formulation administered at the same dosage; (2) a $C_{max}$ for glipizide, when assayed in the plasma of a mammalian subject following administration, that is preferably greater than the $C_{max}$ for a non-nanoparticulate glipizide formulation administered at the same dosage; and/or (3) an AUC for glipizide, when assayed in the plasma of a mammalian subject following administration, that is preferably greater than the AUC for a non-nanoparticulate glipizide formulation administered at the same dosage.

The desirable pharmacokinetic profile, as used herein, is the pharmacokinetic profile measured after the initial dose of glipizide. The compositions can be formulated in any way as described below and as known to those of skill in the art.

A preferred glipizide composition of the invention exhibits in comparative pharmacokinetic testing with a non-nanoparticulate glipizide formulation administered at the same dosage, a $T_{max}$ not greater than about 90%, not greater than about 80%, not greater than about 70%, not greater than about 60%, not greater than about 50%, not greater than about 30%, not greater than about 25%, not greater than about 20%, not greater than about 15%, not greater than about 10%, or not greater than about 5% of the $T_{max}$ exhibited by the non-nanoparticulate glipizide formulation.

This shorter $T_{max}$ translates into a faster onset of therapeutic activity. The use of conventional formulations of glipizide is not ideal due to delayed onset of action. Specifically, conventional glipizide formulations exhibit a peak plasma concentration at 1-3 hours following administration. In contrast, the nanoparticulate glipizide compositions of the invention exhibit faster therapeutic effects.

A preferred glipizide composition of the invention exhibits in comparative pharmacokinetic testing with a non-nanoparticulate glipizide formulation of administered at the same dosage, a $C_{max}$ which is at least about 50%, at least about 100%, at least about 200%, at least about 300%, at least about 400%, at least about 500%, at least about 600%, at least about 700%, at least about 800%, at least about 900%, at least about 1000%, at least about 1100%, at least about 1200%, at least about 1300%, at least about 1400%, at least about 1500%, at least about 1600%, at least about 1700%, at least about 1800%, or at least about 1900% greater than the $C_{max}$ exhibited by the non-nanoparticulate glipizide formulation.

A preferred glipizide composition of the invention exhibits in comparative pharmacokinetic testing with a non-nanoparticulate glipizide formulation administered at the same dosage, an AUC which is at least about 25%, at least about 50%, at least about 75%, at least about 100%, at least about 125%, at least about 150%, at least about 175%, at least about 200%, at least about 225%, at least about 250%, at least about 275%, at least about 300%, at least about 350%, at least about 400%, at least about 450%, at least about 500%, at least about 550%, at least about 600%, at least about 750%, at least about 700%, at least about 750%, at least about 800%, at least about 850%, at least about 900%, at least about 950%, at least about 1000%, at least about 1050%, at least about 1100%, at least about 1150%, or at least about 1200% greater than the AUC exhibited by the non-nanoparticulate glipizide formulation.

Any formulation giving the desired pharmacokinetic profile is suitable for administration according to the present methods. Exemplary types of formulations giving such profiles are liquid dispersions, gels, aerosols, ointments, creams, solid dose forms, etc. of nanoparticulate glipizide.

C. The Pharmacokinetic Profiles of the Nanoparticulate Glipizide Compositions of the Invention are Preferably not Substantially Affected by the Fed or Fasted State of the Subject Ingesting the Compositions The invention encompasses nanoparticulate glipizide compositions wherein preferably the pharmacokinetic profile of the glipizide is not substantially affected by the fed or fasted state of a subject ingesting the composition. This means that there is no substantial difference in the quantity of glipizide absorbed or the rate of glipizide absorption when the nanoparticulate glipizide compositions are administered in the fed versus the fasted state. Thus, the nanoparticulate glipizide compositions of the invention can substantially eliminate the effect of food on the pharmacokinetics of glipizide.

In another embodiment of the invention, the pharmacokinetic profile of the glipizide compositions of the invention, when administered to a mammal in a fasted state, is bioequivalent to the pharmacokinetic profile of the same glipizide composition administered at the same dosage, when administered to a mammal in a fed state. "Bioequivalency" is preferably established by a 90% Confidence Interval (CI) of between 0.80 and 1.25 for both $C_{max}$ and AUC under U.S. Food and Drug Administration (USFDA) regulatory guidelines, or a 90% CI for AUC of between 0.80 to 1.25 and a 90% CI for $C_{max}$ of between 0.70 to 1.43 under the European Medicines Evaluation Agency (EMEA) regulatory guidelines ($T_{max}$ is not relevant for bioequivalency determinations under USFDA and EMEA regulatory guidelines).

Preferably the difference in AUC (e.g., absorption) of the nanoparticulate glipizide composition of the invention, when administered in the fed versus the fasted state, is less than about 100%, less than about 90%, less than about 80%, less than about 70%, less than about 60%, less than about 50%, less than about 40%, less than about 35%, less than about 30%, less than about 25%, less than about 20%, less than about 15%, less than about 10%, less than about 5%, or less than about 3%.

In addition, preferably the difference in $C_{max}$ of the nanoparticulate glipizide composition of the invention, when administered in the fed versus the fasted state, is less than about 100%, less than about 90%, less than about 80%, less than about 70%, less than about 60%, less than about 50%, less than about 40%, less than about 35%, less than about 30%, less than about 25%, less than about 20%, less than about 15%, less than about 10%, less than about 5%, or less than about 3%.

Finally, preferably the difference in the $T_{max}$ of the nanoparticulate glipizide compositions of the invention, when administered in the fed versus the fasted state, is less than about 100%, less than about 90%, less than about 80%, less than about 70%, less than about 60%, less than about 50%, less than about 40%, less than about 30%, less than about 20%, less than about 15%, less than about 10%, less than about 5%, less than about 3%, or essentially no difference.

Benefits of a dosage form that substantially eliminates the effect of food include an increase in subject convenience, thereby increasing subject compliance, as the subject does not need to ensure that they are taking a dose either with or without food.

D. Redispersibility Profiles of the Nanoparticulate Glipizide Compositions of the Invention An additional feature of the nanoparticulate glipizide compositions of the invention is that the compositions redisperse such that the effective average particle size of the redispersed glipizide particles is less than about 2 microns. This is significant, as if upon administration the nanoparticulate glipizide particles present in the compositions of the invention did not redisperse to a substantially nanoparticulate particle size, then the dosage form may lose the benefits afforded by formulating glipizide into a nanoparticulate particle size.

This is because nanoparticulate glipizide compositions benefit from the small particle size of glipizide; if the nanoparticulate glipizide particles do not redisperse into the small particle sizes upon administration, then "clumps" or agglomerated glipizide particles are formed. With the formation of such agglomerated particles, the bioavailability of the dosage form may fall.

Moreover, the nanoparticulate glipizide compositions of the invention exhibit dramatic redispersion of the glipizide particles upon administration to a mammal, such as a human or animal, as demonstrated by reconstitution in a biorelevant aqueous media. Such biorelevant aqueous media can be any aqueous media that exhibit the desired ionic strength and pH, which form the basis for the biorelevance of the media. The desired pH and ionic strength are those that are representative of physiological conditions found in the human body. Such biorelevant aqueous media can be, for example, aqueous electrolyte solutions or aqueous solutions of any salt, acid, or base, or a combination thereof, which exhibit the desired pH and ionic strength.

Biorelevant pH is well known in the art. For example, in the stomach, the pH ranges from slightly less than 2 (but typically greater than 1) up to 4 or 5. In the small intestine the pH can range from 4 to 6, and in the colon it can range from 6 to 8. Biorelevant ionic strength is also well known in the art. Fasted state gastric fluid has an ionic strength of about 0.1M while fasted state intestinal fluid has an ionic strength of about 0.14.

See e.g., Lindahl et al., "Characterization of Fluids from the Stomach and Proximal Jejunum in Men and Women," *Pharm. Res.*, 14 (4): 497-502 (1997).

It is believed that the pH and ionic strength of the test solution is more critical than the specific chemical content. Accordingly, appropriate pH and ionic strength values can be obtained through numerous combinations of strong acids, strong bases, salts, single or multiple conjugate acid-base pairs (i.e., weak acids and corresponding salts of that acid), monoprotic and polyprotic electrolytes, etc.

Representative electrolyte solutions can be, but are not limited to, HCl solutions, ranging in concentration from about 0.001 to about 0.1 M, and NaCl solutions, ranging in concentration from about 0.001 to about 0.1 M, and mixtures thereof. For example, electrolyte solutions can be, but are not limited to, about 0.1 M HCl or less, about 0.01 M HCl or less, about 0.001 M HCl or less, about 0.1 M NaCl or less, about 0.01 M NaCl or less, about 0.001 M NaCl or less, and mixtures thereof. Of these electrolyte solutions, 0.01 M HCl and/or 0.1 M NaCl, are most representative of fasted human physiological conditions, owing to the pH and ionic strength conditions of the proximal gastrointestinal tract.

Electrolyte concentrations of 0.001 M HCl, 0.01 M HCl, and 0.1 M HCl correspond to pH 3, pH 2, and pH 1, respectively. Thus, a 0.01 M HCl solution simulates typical acidic conditions found in the stomach. A solution of 0.1 M NaCl provides a reasonable approximation of the ionic strength conditions found throughout the body, including the gastrointestinal fluids, although concentrations higher than 0.1 M may be employed to simulate fed conditions within the human GI tract.

Exemplary solutions of salts, acids, bases or combinations thereof, which exhibit the desired pH and ionic strength, include but are not limited to phosphoric acid/phosphate salts+sodium, potassium and calcium salts of chloride, acetic acid/acetate salts+sodium, potassium and calcium salts of chloride, carbonic acid/bicarbonate salts+sodium, potassium and calcium salts of chloride, and citric acid/citrate salts+sodium, potassium and calcium salts of chloride.

In other embodiments of the invention, the redispersed glipizide particles of the invention (redispersed in an aqueous, biorelevant, or any other suitable media) have an effective average particle size of less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

Redispersibility can be tested using any suitable means known in the art. See e.g., the example sections of U.S. Pat. No. 6,375,986 for "Solid Dose Nanoparticulate Compositions Comprising a Synergistic Combination of a Polymeric Surface Stabilizer and Dioctyl Sodium Sulfosuccinate."

E. Bioadhesive Nanoparticulate Glipizide Compositions

Bioadhesive nanoparticulate glipizide compositions of the invention comprise at least one cationic surface stabilizer, which are described in more detail below. Bioadhesive formulations of glipizide exhibit exceptional bioadhesion to biological surfaces, such as mucous.

In the case of bioadhesive nanoparticulate glipizide compositions, the term "bioadhesion" is used to describe the adhesion between the nanoparticulate glipizide compositions and a biological substrate (i.e., gastrointestinal mucin, lung tissue, nasal mucosa, etc.). See e.g., U.S. Pat. No. 6,428,814 for "Bioadhesive Nanoparticulate Compositions Having Cationic Surface Stabilizers," which is specifically incorporated by reference.

The bioadhesive glipizide compositions of the invention are useful in any situation in which it is desirable to apply the compositions to a biological surface. The bioadhesive glipizide compositions preferably coat the targeted surface in a continuous and uniform film that is invisible to the naked human eye.

A bioadhesive nanoparticulate glipizide composition slows the transit of the composition, and some glipizide particles would also most likely adhere to tissue other than the mucous cells and therefore give a prolonged exposure to glipizide, thereby increasing absorption and the bioavailability of the administered dosage.

F. Low Viscosity

A liquid dosage form of a conventional microcrystalline or non-nanoparticulate glipizide composition would be expected to be a relatively large volume, highly viscous substance which would not be well accepted by patient populations. Moreover, viscous solutions can be problematic in parenteral administration because these solutions require a slow syringe push and can stick to tubing. In addition, conventional formulations of poorly water-soluble active agents, such as glipizide, tend to be unsafe for intravenous administration techniques, which are used primarily in conjunction with highly water-soluble substances.

Liquid dosage forms of the nanoparticulate glipizide compositions of the invention provide significant advantages over a liquid dosage form of a conventional microcrystalline or solubilized glipizide composition. The low viscosity and silky texture of liquid dosage forms of the nanoparticulate glipizide compositions of the invention result in advantages in both preparation and use. These advantages include, for example: (1) better subject compliance due to the perception of a lighter formulation which is easier to consume and digest; (2) ease of dispensing because one can use a cup or a syringe; (3) potential for formulating a higher concentration of glipizide resulting in a smaller dosage volume and thus less volume for the subject to consume; and (4) easier overall formulation concerns.

Liquid glipizide dosage forms that are easier to consume are especially important when considering juvenile patients, terminally ill patients, and elderly patients. Viscous or gritty formulations, and those that require a relatively large dosage volume, are not well tolerated by these patient populations. Liquid oral dosage forms can be particularly preferably for patient populations who have difficulty consuming tablets, such as infants and the elderly.

The viscosities of liquid dosage forms of nanoparticulate glipizide according to the invention are preferably less than about $1/200$, less than about $1/175$, less than about $1/150$, less than about $1/125$, less than about $1/100$, less than about $1/75$, less than about $1/50$, or less than about $1/25$ of a liquid oral dosage form of a non-nanoparticulate glipizide composition, at about the same concentration per ml of glipizide.

Typically the viscosity of liquid nanoparticulate glipizide dosage forms of the invention, at a shear rate of 0.1 (1/s) measured at 20° C., is from about 2000 mPa·s to about 1 mPa·s, from about 1900 mPa·s to about 1 mPa·s, from about 1800 mPa·s to about 1 mPa·s, from about 1700 mPa·s to about 1 mPa·s, from about 1600 mPa·s to about 1 mPa·s, from about 1500 mPa·s to about 1 mPa·s, from about 1400 mPa·s to about 1 mPa·s, from about 1300 mPa·s to about 1 mPa·s, from about 1200 mPa·s to about 1 mPa·s, from about 1100 mPa·s to about 1 mPa·s, from about 1000 mPa·s to about 1 mPa·s, from about 900 mPa·s to about 1 mPa·s, from about 800 mPa·s to about 1 mPa·s, from about 700 mPa·s to about 1 mPa·s, from about 600 mPa·s to about 1 mPa·s, from about 500 mPa·s to about 1 mPa·s, from about 400 mPa·s to about 1 mPa·s, from about 300 mPa·s to about 1 mPa·s, from about 200 mPa·s to about 1 mPa·s, from about 175 mPa·s to about 1 mPa·s, from about 150 mPa·s to about 1 mPa·s, from about 125 mPa·s to about 1 mPa·s, from about 100 mPa·s to about 1 mPa·s, from about 75 mPa·s to about 1 mPa·s, from about 50 mPa·s to about 1 mPa·s, from about 25 mPa·s to about 1 mPa·s, from about 15 mPa·s to about 1 mPa·s, from about 10 mPa·s to about 1 mPa·s, or from about 5 mPa·s to about 1 mPa·s. Such a viscosity is much more attractive for subject consumption and may lead to better overall subject compliance.

Viscosity is concentration and temperature dependent. Typically, a higher concentration results in a higher viscosity, while a higher temperature results in a lower viscosity. Viscosity as defined above refers to measurements taken at about 20° C. (The viscosity of water at 20° C. is 1 mPa·s.) The invention encompasses equivalent viscosities measured at different temperatures.

Another important aspect of the invention is that the nanoparticulate glipizide compositions of the invention, formulated into a liquid dosage form, are not turbid. "Turbid," as used herein refers to the property of particulate matter that can be seen with the naked eye or that which can be felt as "gritty." The nanoparticulate glipizide compositions of the invention, formulated into a liquid dosage form, can be poured out of or extracted from a container as easily as water, whereas a liquid dosage form of a non-nanoparticulate or solubilized glipizide is expected to exhibit notably more "sluggish" characteristics.

The liquid formulations of this invention can be formulated for dosages in any volume but preferably equivalent or smaller volumes than a liquid dosage form of a non-nanoparticulate glipizide composition.

G. Sterile Filtered Nanoparticulate Glipizide Compositions

The nanoparticulate glipizide compositions of the invention can be sterile filtered. This obviates the need for heat sterilization, which can harm or degrade glipizide, as well as result in crystal growth and particle aggregation.

Sterile filtration can be difficult because of the required small particle size of the composition. Filtration is an effective method for sterilizing homogeneous solutions when the membrane filter pore size is less than or equal to about 0.2 microns (200 nm) because a 0.2 micron filter is sufficient to remove essentially all bacteria. Sterile filtration is normally not used to sterilize suspensions of micron-sized glipizide because the glipizide particles are too large to pass through the membrane pores.

A sterile nanoparticulate glipizide dosage form is particularly useful in treating immunocompromised patients, infants or juvenile patients, and the elderly, as these patient groups are the most susceptible to infection caused by a non-sterile liquid dosage form.

Because the nanoparticulate glipizide compositions of the invention, formulated into a liquid dosage form, can be sterile filtered, and because the compositions can have a very small glipizide effective average particle size, the compositions are suitable for parenteral administration.

H. Combination Pharmacokinetic Profile Compositions

In yet another embodiment of the invention, a first nanoparticulate glipizide composition providing a desired pharmacokinetic profile is co-administered, sequentially administered, or combined with at least one other glipizide composition that generates a desired different pharmacokinetic profile. More than two glipizide compositions can be co-administered, sequentially administered, or combined. While the first glipizide composition has a nanoparticulate particle size, the additional one or more glipizide compositions can be nanoparticulate, solubilized, or have a microparticulate particle size.

For example, a first glipizide composition can have a nanoparticulate particle size, conferring a short $T_{max}$ and typically a higher $C_{max}$. This first glipizide composition can be combined, co-administered, or sequentially administered with a second composition comprising: (1) glipizide having a larger (but still nanoparticulate as defined herein) particle size, and therefore exhibiting slower absorption, a longer $T_{max}$, and typically a lower $C_{max}$; or (2) a microparticulate or solubilized glipizide composition, exhibiting a longer $T_{max}$, and typically a lower $C_{max}$.

The second, third, fourth, etc., glipizide compositions can differ from the first, and from each other, for example: (1) in the effective average particle sizes of glipizide; or (2) in the dosage of glipizide. Such a combination composition can reduce the dose frequency required.

If the second glipizide composition has a nanoparticulate particle size, then preferably the glipizide particles of the second composition have at least one surface stabilizer associated with the surface of the drug particles. The one or more surface stabilizers can be the same as or different from the surface stabilizer(s) present in the first glipizide composition.

Preferably where co-administration of a "fast-acting" formulation and a "longer-lasting" formulation is desired, the two formulations are combined within a single composition, for example a dual-release composition.

I. Combination Active Agent Compositions

The invention encompasses the nanoparticulate glipizide compositions of the invention formulated or co-administered with one or more non-glipizide active agents. Methods of using such combination compositions are also encompassed by the invention. The non-glipizide active agents can be present in a crystalline phase, an amorphous phase, a semi-crystalline phase, a semi-amorphous phase, or a mixture thereof.

The compound to be administered in combination with a nanoparticulate glipizide composition of the invention can be formulated separately from the nanoparticulate glipizide composition or co-formulated with the nanoparticulate glipizide composition. Where a nanoparticulate glipizide composition is co-formulated with a second active agent, the second active agent can be formulated in any suitable manner, such as immediate-release, rapid-onset, sustained-release, or dual-release form.

Such non-glipizide active agents can be, for example, a therapeutic agent. A therapeutic agent can be a pharmaceutical agent, including a biologic. The active agent can be selected from a variety of known classes of drugs, including, for example, amino acids, proteins, peptides, nucleotides, anti-obesity drugs, central nervous system stimulants, carotenoids, corticosteroids, elastase inhibitors, anti-fungals, oncology therapies, anti-emetics, analgesics, cardiovascular agents, anti-inflammatory agents, such as NSAIDs and COX-2 inhibitors, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives (hypnotics and neuroleptics), astringents, alpha-adrenergic receptor blocking agents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators, and xanthines.

Examples of representative active agents useful in this invention include, but are not limited to, acyclovir, alprazolam, altretamine, amiloride, amiodarone, benztropine mesylate, bupropion, cabergoline, candesartan, cerivastatin, chlorpromazine, ciprofloxacin, cisapride, clarithromycin, clonidine, clopidogrel, cyclobenzaprine, cyproheptadine, delavirdine, desmopressin, diltiazem, dipyridamole, dolasetron, enalapril maleate, enalaprilat, famotidine, felodipine, furazolidone, irbesartan, ketoconazole, lansoprazole, loratadine, loxapine, mebendazole, mercaptopurine, milrinone lactate, minocycline, mitoxantrone, nelfinavir mesylate, nimodipine, norfloxacin, olanzapine, omeprazole, penciclovir, pimozide, tacolimus, quazepam, raloxifene, rifabutin, rifampin, risperidone, rizatriptan, saquinavir, sertraline, sildenafil, acetyl-sulfisoxazole, temazepam, thiabendazole, thioguanine, trandolapril, triamterene, trimetrexate, troglitazone, trovafloxacin, verapamil, vinblastine sulfate, mycophenolate, atovaquone, atovaquone, proguanil, ceftazidime, cefuroxime, etoposide, terbinafine, thalidomide, fluconazole, amsacrine, dacarbazine, teniposide, and acetylsalicylate.

A description of these classes of active agents and a listing of species within each class can be found in Martindale's *The Extra Pharmacopoeia*, 31$^{st}$ Edition (The Pharmaceutical Press, London, 1996), specifically incorporated by reference. The active agents are commercially available and/or can be prepared by techniques known in the art.

Exemplary nutraceuticals or dietary supplements include, but are not limited to, lutein, folic acid, fatty acids (e.g., DHA and ARA), fruit and vegetable extracts, vitamin and mineral supplements, phosphatidylserine, lipoic acid, melatonin, glucosamine/chondroitin, Aloe Vera, Guggul, glutamine, amino acids (e.g., arginine, iso-leucine, leucine, lysine, methionine, phenylanine, threonine, tryptophan, and valine), green tea, lycopene, whole foods, food additives, herbs, phytonutrients, antioxidants, flavonoid constituents of fruits, evening primrose oil, flax seeds, fish and marine animal oils, and probiotics. Nutraceuticals and dietary supplements also include bioengineered foods genetically engineered to have a desired property, also known as "pharmafoods."

Exemplary nutraceuticals and dietary supplements are disclosed, for example, in Roberts et al., *Nutraceuticals: The Complete Encyclopedia of Supplements, Herbs, Vitamins, and Healing Foods* (American Nutraceutical Association, 2001), which is specifically incorporated by reference. Dietary supplements and nutraceuticals are also disclosed in *Physicians' Desk Reference for Nutritional Supplements*, 1st Ed. (2001) and The *Physicians' Desk Reference for Herbal Medicines*, 1st Ed. (2001), both of which are also incorporated by reference. A nutraceutical or dietary supplement, also known as a phytochemical or functional food, is generally any one of a class of dietary supplements, vitamins, minerals, herbs, or healing foods that have medical or pharmaceutical effects on the body.

J. Miscellaneous Benefits of the Nanoparticulate Glipizide Compositions of the Invention The nanoparticulate glipizide compositions preferably exhibit an increased rate of dissolution as compared to microcrystalline or non-nanoparticulate forms of glipizide. In addition, the nanoparticulate glipizide compositions preferably exhibit improved performance characteristics for oral, intravenous, subcutaneous, or intramuscular injection, such as higher dose loading and smaller tablet or liquid dose volumes. Moreover, the nanoparticulate glipizide compositions of the invention do not require organic solvents or pH extremes.

II. Glipizide Compositions

The invention provides compositions comprising nanoparticulate glipizide particles and at least one surface stabilizer. The surface stabilizers are preferably associated with the surface of the glipizide particles. Surface stabilizers useful herein do not chemically react with the glipizide particles or itself. Preferably, individual molecules of the surface stabilizer are essentially free of intermolecular cross-linkages. The compositions can comprise two or more surface stabilizers.

The present invention also includes nanoparticulate glipizide compositions together with one or more non-toxic physiologically acceptable carriers, adjuvants, or vehicles, collectively referred to as carriers. The compositions can be formulated for parenteral injection (e.g., intravenous, intramuscular, or subcutaneous), oral administration (in solid, liquid, or aerosol (i.e., pulmonary) form), vaginal, nasal, rectal, ocular, local (powders, creams, ointments or drops), buccal, intracisternal, intraperitoneal, topical administration, and the like.

A. Glipizide Particles

As used herein, "glipizide" means 1-cyclohexyl-3-[[p-[2-(5-methylpyrazinecarboxamido)ethyl]-phenyl]sulfonyl]urea or a salt thereof, and having the following chemical structure:

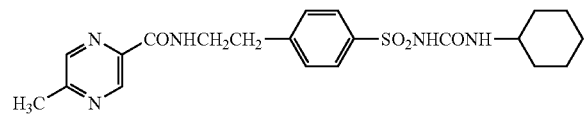

Derivatives of glipizide are also encompassed by the term "glipizide."

Glipizide is an oral antidiabetic medication used to treat type 2 (non-insulin-dependent) diabetes. Without being bound to any one theory, the mode of action of glipizide in animal models appears to be stimulation of insulin secretion from the beta cells of the pancreatic islet tissue and is thus dependent on functioning beta cells in the pancreatic islets. In humans, glipizide appears to lower the blood glucose acutely by stimulating the release of insulin form the pancreas, an effect dependent upon functioning beta cells in the pancreatic islets.

Glipizide can be in a crystalline phase, an amorphous phase, a semi-crystalline phase, a semi-amorphous phase, or a mixture thereof.

B. Surface Stabilizers

The choice of a surface stabilizer for glipizide is non-trivial and required extensive experimentation to realize a desirable formulation. Accordingly, the present invention is directed to the surprising discovery that nanoparticulate glipizide compositions can be made.

Combinations of more than one surface stabilizer can be used in the invention. Useful surface stabilizers that can be employed in the invention include, but are not limited to, known organic and inorganic pharmaceutical excipients.

Such excipients include various polymers, low molecular weight oligomers, natural products, and surfactants. Surface stabilizers include nonionic, anionic, cationic, zwitterionic, and ionic surfactants.

Representative examples of other useful surface stabilizers include hydroxypropyl methylcellulose, hydroxypropylcellulose, polyvinylpyrrolidone, sodium lauryl sulfate, dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxs 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hydroxypropylmethylcellulose phthalate, noncrystalline cellulose, magnesium aluminium silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); Tetronic 1508® (T-1508) (BASF Wyandotte Corporation), Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-1OG® or Surfactant 10-G® (Olin Chemicals, Stamford, Conn.); Crodestas SL-40® (Croda, Inc.); and SA90HCO, which is $C_{18}H_{37}CH_2(CON(CH_3)-CH_2(CHOH)_4(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-derivatized phospholipid, PEG-derivatized cholesterol, PEG-derivatized cholesterol derivative, PEG-derivatized vitamin A, PEG-derivatized vitamin E, lysozyme, random copolymers of vinyl pyrrolidone and vinyl acetate, and the like.

Depending upon the desired method of administration, bioadhesive formulations of nanoparticulate glipizide can be prepared by selecting one or more cationic surface stabilizers that impart bioadhesive properties to the resultant composition. Useful cationic surface stabilizers are described below.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), polyvinylpyrrolidone-2-dimethylaminoethyl methacrylate dimethyl sulfate, 1,2 Dipalmitoyl-sn-Glycero-3-Phosphoethanolamine-N-[Amino(Polyethylene Glycol)2000] (sodium salt) (also known as DPPE-PEG (2000)-Amine Na) (Avanti Polar Lipids, Alabaster, Ala.), Poly(2-methacryloxyethyl trimethylammonium bromide) (Polysciences, Inc., Warrington, Pa.) (also known as S1001), poloxamines such as Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.), lysozyme, long-chain polymers such as alginic acid, carrageenan (FMC Corp.), and POLYOX (Dow, Midland, Mich.).

Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl ($C_{12-18}$)dimethylbenzyl ammonium chloride, N-alkyl ($C_{14-18}$) dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($Cl_{12-14}$) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ and ALKAQUAT™ (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly [diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological*

*Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Nonpolymeric cationic surface stabilizers are any nonpolymeric compound, such as benzalkonium chloride, a carbonium compound, a phosphonium compound, an oxonium compound, a halonium compound, a cationic organometallic compound, a quarternary phosphorous compound, a pyridinium compound, an anilinium compound, an ammonium compound, a hydroxylammonium compound, a primary ammonium compound, a secondary ammonium compound, a tertiary ammonium compound, and quarternary ammonium compounds of the formula $NR_1R_2R_3R_4^{(+)}$. For compounds of the formula $NR_1R_2R_3R_4^{(+)}$:

(i) none of $R_1$-$R_4$ are $CH_3$;
(ii) one of $R_1$-$R_4$ is $CH_3$;
(iii) three of $R_1$-$R_4$ are $CH_3$;
(iv) all of $R_1$-$R_4$ are $CH_3$;
(v) two of $R_1$-$R_4$ are $CH_3$, one of $R_1$-$R_4$ is $C_6H_5CH_2$, and one of $R_1$-$R_4$ is an alkyl chain of seven carbon atoms or less;
(vi) two of $R_1$-$R_4$ are $CH_3$, one of $R_1$-$R_4$ is $C_6H_5CH_2$, and one of $R_1$-$R_4$ is an alkyl chain of nineteen carbon atoms or more;
(vii) two of $R_1$-$R_4$ are $CH_3$ and one of $R_1$-$R_4$ is the group $C_6H_5(CH_2)_n$, where n>1;
(viii) two of $R_1$-$R_4$ are $CH_3$, one of $R_1$-$R_4$ is $C_6H_5CH_2$, and one of $R_1$-$R_4$ comprises at least one heteroatom;
(ix) two of $R_1$-$R_4$ are $CH_3$, one of $R_1$-$R_4$ is $C_6H_5CH_2$, and one of $R_1$-$R_4$ comprises at least one halogen;
(x) two of $R_1$-$R_4$ are $CH_3$, one of $R_1$-$R_4$ is $C_6H_5CH_2$, and one of $R_1$-$R_4$ comprises at least one cyclic fragment;
(xi) two of $R_1$-$R_4$ are $CH_3$ and one of $R_1$-$R_4$ is a phenyl ring; or
(xii) two of $R_1$-$R_4$ are $CH_3$ and two of $R_1$-$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3) oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Surface stabilizers useful in the present invention include those listed above, but excluding cyclodextrin and cyclodextrin derivatives.

A preferred surface stabilizer is hydroxypropyl cellulose (HPC).

Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference.

C. Pharmaceutical Excipients

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™).

Suitable lubricants, including agents that act on the flowability of the powder to be compressed, are colloidal silicon dioxide, such as Aerosil® 200, talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

D. Nanoparticulate Glipizide Particle Size

As used herein, particle size is determined on the basis of the weight average particle size as measured by conventional particle size measuring techniques well known to those skilled in the art. Such techniques include, for example, sedimentation field flow fractionation, photon correlation spectroscopy, light scattering, and disk centrifugation.

The compositions of the invention comprise glipizide nanoparticles which have an effective average particle size of less than about 2000 nm (i.e., 2 microns), less than about 1900 nm, less than less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 140 nm, less than about 130 nm, less than about 120 nm, less than about 110 nm, less than about 100 nm, less than about 90 nm, less than about 80 nm, less than about 70 nm, less than about 60 nm, or less than about 50 nm, when measured by the above-noted techniques.

By "an effective average particle size of less than about 2000 nm" it is meant that at least 50% of the nanoparticulate glipizide particles have a weight average particle size less than about 2000 nm, when measured by the above-noted techniques. In other embodiments of the invention, at least about 70%, at least about 90%, at least about 95%, or at least about 99% of the glipizide particles have a particle size less than the effective average, by weight, i.e., less than about 2000 nm, less than about 1900 nm, less than less than about 1800 nm, less than about 1700 nm, etc.

If the nanoparticulate glipizide composition is combined with a microparticulate glipizide or non-glipizide active agent composition, then such a composition is either solubilized or has an effective average particle size greater than about 2 microns. By "an effective average particle size of greater than about 2 microns" it is meant that at least 50% of the microparticulate glipizide or non-glipizide active agent particles have a particle size greater than about 2 microns, by weight, when measured by the above-noted techniques. In other embodiments of the invention, at least about 70%, at least about 90%, at least about 95%, or at least about 99%, by weight, of the microparticulate glipizide or non-glipizide active agent particles have a particle size greater than about 2 microns.

In the present invention, the value for D50 of a nanoparticulate glipizide composition is the particle size below which 50% of the glipizide particles fall, by weight. Similarly, D90 and D99 are the particle sizes below which 90% and 99%, respectively, of the glipizide particles fall, by weight.

E. Concentration of Nanoparticulate Glipizide and Surface Stabilizers

The relative amounts of glipizide and one or more surface stabilizers can vary widely. The optimal amount of the individual components can depend, for example, upon the hydrophilic lipophilic balance (HLB), melting point, and the surface tension of water solutions of the stabilizer, etc.

The concentration of glipizide can vary from about 99.5% to about 0.001%, from about 95% to about 0.1%, or from about 90% to about 0.5%, by weight, based on the total combined dry weight of the glipizide and at least one surface stabilizer, not including other excipients.

The concentration of the at least one surface stabilizer can vary from about 0.5% to about 99.999%, from about 5.0% to about 99.9%, or from about 10% to about 99.5%, by weight, based on the total combined dry weight of the glipizide and at least one surface stabilizer, not including other excipients.

III. Methods of Making Nanoparticulate Glipizide Formulations

The nanoparticulate glipizide compositions can be made using, for example, milling, homogenization, or precipitation techniques. Exemplary methods of making nanoparticulate compositions are described in the '684 patent. Methods of making nanoparticulate compositions are also described in U.S. Pat. No. 5,518,187 for "Method of Grinding Pharmaceutical Substances;" U.S. Pat. No. 5,718,388 for "Continuous Method of Grinding Pharmaceutical Substances;" U.S. Pat. No. 5,862,999 for "Method of Grinding Pharmaceutical Substances;" U.S. Pat. No. 5,665,331 for "Co-Microprecipitation of Nanoparticulate Pharmaceutical Agents with Crystal Growth Modifiers;" U.S. Pat. No. 5,662,883 for "Co-Microprecipitation of Nanoparticulate Pharmaceutical Agents with Crystal Growth Modifiers;" U.S. Pat. No. 5,560,932 for "Microprecipitation of Nanoparticulate Pharmaceutical Agents;" U.S. Pat. No. 5,543,133 for "Process of Preparing X-Ray Contrast Compositions Containing Nanoparticles;" U.S. Pat. No. 5,534,270 for "Method of Preparing Stable Drug Nanoparticles;" U.S. Pat. No. 5,510,118 for "Process of Preparing Therapeutic Compositions Containing Nanoparticles;" and U.S. Pat. No. 5,470,583 for "Method of Preparing Nanoparticle Compositions Containing Charged Phospholipids to Reduce Aggregation," all of which are specifically incorporated by reference.

Following milling, homogenization, precipitation, etc., the resultant nanoparticulate glipizide composition can be utilized in solid or liquid dosage formulations, such as controlled release formulations, solid dose fast melt formulations, aerosol formulations, nasal formulations, lyophilized formulations, tablets, capsules, solid lozenge, powders, creams, ointments, etc.

A. Milling to Obtain Nanoparticulate Glipizide Dispersions

Milling glipizide to obtain a nanoparticulate dispersion comprises dispersing glipizide particles in a liquid dispersion media in which glipizide is poorly soluble, followed by applying mechanical means in the presence of grinding media to reduce the particle size of glipizide to the desired effective average particle size. The dispersion media can be, for example, water, safflower oil, ethanol, t-butanol, glycerin, polyethylene glycol (PEG), hexane, or glycol.

The glipizide particles can be reduced in size in the presence of at least one surface stabilizer. Alternatively, the glipizide particles can be contacted with one or more surface stabilizers after attrition. Other compounds, such as a diluent, can be added to the glipizide/surface stabilizer composition during the size reduction process. Dispersions can be manufactured continuously or in a batch mode.

B. Precipitation to Obtain Nanoparticulate Glipizide Compositions

Another method of forming the desired nanoparticulate glipizide composition is by microprecipitation. This is a method of preparing stable dispersions of poorly soluble active agents in the presence of one or more surface stabilizers and one or more colloid stability enhancing surface active agents free of any trace toxic solvents or solubilized heavy metal impurities. Such a method comprises, for example: (1) dissolving glipizide in a suitable solvent; (2) adding the formulation from step (1) to a solution comprising at least one surface stabilizer; and (3) precipitating the formulation from step (2) using an appropriate non-solvent. The method can be followed by removal of any formed salt, if present, by dialysis or diafiltration and concentration of the dispersion by conventional means.

C. Homogenization to Obtain Nanoparticulate Glipizide Compositions

Exemplary homogenization methods of preparing active agent nanoparticulate compositions are described in U.S. Pat. No. 5,510,118, for "Process of Preparing Therapeutic Compositions Containing Nanoparticles."

Such a method comprises dispersing glipizide particles in a liquid dispersion media in which glipizide is poorly soluble, followed by subjecting the dispersion to homogenization to reduce the particle size of the glipizide to the desired effective average particle size. The dispersion media can be, for example, water, safflower oil, ethanol, t-butanol, glycerin, polyethylene glycol (PEG), hexane, or glycol.

The glipizide particles can be reduced in size in the presence of at least one surface stabilizer. Alternatively, the glipizide particles can be contacted with one or more surface stabilizers either before or after attrition. Other compounds, such as a diluent, can be added to the glipizide/surface stabilizer composition either before, during, or after the size reduction process. Dispersions can be manufactured continuously or in a batch mode.

IV. Methods of Using Nanoparticulate Glipizide Formulations

The method of the invention comprises administering to a subject an effective amount of a composition comprising nanoparticulate glipizide. The glipizide compositions of the present invention can be administered to a subject via any conventional means including, but not limited to, orally, rectally, ocularly, parenterally (e.g., intravenous, intramuscular, or subcutaneous), intracisternally, pulmonary, intravaginally, intraperitoneally, locally (e.g., powders, ointments or drops), or as a buccal or nasal spray. As used herein, the term "subject" is used to mean an animal, preferably a mammal, including a human or non-human. The terms patient and subject may be used interchangeably.

The USFDA has approved drugs for diabetes, such as glipizide, as adjuncts to controlling diet and exercising for management of diabetes. Some patients usually respond rapidly to control of diet and exercise, however, a blood-glucose lowering drug may be useful when there is uncontrollable blood glucose levels. In contrast, severe cases of non-insulin dependent diabetes mellitus, diet and exercise alone or in combination with a blood glucose lowering drug are frequently prescribed.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The nanoparticulate compositions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration include, but are not limited to, powder aerosols, capsules, tablets, pills, powders, and granules. In such solid dosage forms, the active agent is admixed with at least one of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable aerosols, emulsions, solutions, suspensions, syrups, and elixirs. In addition to the active agent, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

One of ordinary skill will appreciate that effective amounts of glipizide can be determined empirically and can be employed in pure form or, where such forms exist, in pharmaceutically acceptable salt, ester, or prodrug form. Actual dosage levels of glipizide in the nanoparticulate compositions of the invention may be varied to obtain an amount of glipizide that is effective to obtain a desired therapeutic response for a particular composition and method of administration. The selected dosage level therefore depends upon the desired therapeutic effect, the route of administration, the potency of the administered glipizide, the desired duration of treatment, and other factors.

Dosage unit compositions may contain such amounts of such submultiples thereof as may be used to make up the daily dose. It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex, and diet of the patient; the time of administration, route of administration, and rate of excretion of the agent; the duration of the treatment; drugs used in combination or coincidental with the specific agent; and like factors well known in the medical arts.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

Example 1

The purpose of this example was to prepare a fast melt formulation of nanoparticulate glipizide.

A colloidal dispersion of glipizide in water was prepared having 10% (w/w) glipizide and 2% (w/w) hydroxypropyl cellulose (HPC). Particle size analysis performed using a Malvern Mastersizer S2.14 (Malvern Instruments Ltd., Malvern, Worcestershire, UK) recorded by a wet method showed the following particle size characteristics: $D_{v,10}=270$ nm; $D_{v,50}=400$ nm; and $D_{v,90}=660$ nm.

The nanoparticulate glipizide dispersion was prepared for spray drying by diluting 1:1 with purified water followed by homogenization. Mannitol (10% (w/w)) was then added followed by homogenisation. The mixture obtained was spray-dried using a Buchi Mini B-191 spray drier system (Buchi, Switzerland).

A blend was prepared according to the formulation detailed in Table 1.

TABLE 1

Fast Melt Glipizide Tablets

| Material | % |
| --- | --- |
| Spray dried glipizide | 5.33 |
| Mannitol | 13.47 |
| Xylitol | 40.53 |
| Citric acid | 19.60 |
| Sodium bicarbonate | 19.33 |
| Aspartame ® | 0.28 |
| PEG 4000 | 0.93 |
| Sodium stearyl fumerate | 0.53 |

The mannitol, xylitol, Aspartame®, half of the citric acid, and half of the sodium bicarbonate were mixed in a Uni-glatt (Glatt GmbH, Dresden, Germany). A 10% solution of PEG 4000 was used to granulate the mix at a spray rate of 10 g/min. The resultant granulate was dried for 30 minutes at about 40° C., after which the remainder of the citric acid and sodium bicarbonate, the spray-dried glipizide nanocrystals, and the sodium stearyl fumerate were added and mixed.

The resultant blend was tableted to form glipizide 5 mg tablets using a Piccalo RTS tablet press with 10.0 mm normal concave round tooling (Piccola Industria, Argentina). The tablets produced had a mean tablet weight of 287.91.+−.11.14 mg and a mean hardness of 39.4.+−.8 N. Disintegration testing was carried out in purified water using a VanKel disintegration apparatus (VanKel, Edison, N.J.) at 32 oscillations per min. at 37° C. The average tablet disintegration time was found to be 43 seconds.

Example 2

The purpose of this example was to prepare a nanoparticulate glipizide composition.

Glipizide and HPC-SL in the ratio of 10:3 were milled in a Dyno-mill (Type: KDL; Mfg.: Willy Bachofen, Basel, Switzerland) to produce a nanoparticulate glipizide dispersion. The composition was milled for 6 hours, and the average effective particle size of the glipizde was about 177 nm, with about 50% of the particles having a size less than about 157 nm, and about 90% of the particles having a size less than about 276 nm.

Example 3

The purpose of this example was to prepare a controlled release formulation of glipizide.

The nanoparticulate glipizide dispersion produced in Example 2 was spray dried using a Yamato GB-22® spray-dryer under following conditions to produce a spray-dried glipizide intermediate (SDI):

| | |
| --- | --- |
| Inlet temp.: | 115° C. |
| Outlet temp.: | 50° C. |
| drying air | 0.36 m³/min |
| atomizing air | 2.5 Kgf/cm² |

The powder blend for the tablets comprised: 13 mg SDI, 241.6 mg Methocel® (K100LV), 483.3 mg lactose (Foremost #316), and 12.1 mg magnesium stearate, for a total of 750.0 mg. Each 750.0 mg tablet contained 10 mg of the drug (glipizide)

The excipients were sieved, blended, and compressed using a Carver press at 5,000 lb for 10 sec. The tablets were analyzed (at 274 nm) using the dissolution system as described above.

The results, shown in FIG. 1, indicate a steady release of drug over a time period of just under 16 hours (i.e., about 950 minutes).

Example 4

The purpose of this example was to prepare an uncoated controlled release tablet formulation containing nanoparticulate glipizide.

A colloidal dispersion of glipizide in water was prepared. The dispersion contained 10% (w/w) of the drug and 3% hydroxypropyl cellulose. Particle size analysis, performed using a Malvern Mastersizer S2.14, recorded by a wet method using a 150 ml flow through cell, revealed the following particle size characteristics: $D_{v,90}$ 650 nm; $D_{v,50}$ 386 nm; $D_{v,10}$ 290 nm.

The glipizide dispersion was prepared for spray drying by adding 15% mannitol to the aqueous glipizide dispersion with stirring. The final content of the mixture to be spray dried is given in Table 2.

TABLE 2

Composition prior to spray drying for Example 3

| Ingredient | Amount (% by wt.) |
| --- | --- |
| Glipizide dispersion | 10 |
| Hydroxypropyl cellulose | 3 |
| Mannitol | 15 |
| Purified water | 72 |

The mixture thus obtained was spray dried using a Büchi Mini B-191 Spray Drier system. The spray drying condition are summarized in Table 3.

TABLE 3

Spray drying conditions for Example 3

| Parameter | Level |
| --- | --- |
| Inlet temperature | 115-116° C. |
| Atomising pressure setting | 800 mbar |
| Vacuum pressure | 25-45 mbar |
| Aspirator setting | 100% |
| Spray rate | 10 ml/min |

The spray dried glipizide particles thus prepared were then blended. The blend formulation is given in Table 4.

TABLE 4

Blend formulation for Example 3

| Ingredient | Amount (% by wt.) |
|---|---|
| Spray dried glipizide | 3.36 |
| Avicel ™ pH101 | 35.8 |
| Methocel K ™ 100LV | 60.0 |
| Aerosil ™ 200 | 0.4 |
| Magnesium stearate | 0.5 |

The blend obtained after the previous step was tableted using a single station tablet press fitted with 9.5 mm round normal concave tooling. The tablets produced had a mean tablet hardness of 149 N and a mean tablet potency of 9.1 mg/tablet. In vitro dissolution was carried out in $KH_2PO_4$ buffer, pH 7.5, using USP apparatus I (100 rpm). Dissolution data is given in Table 5.

TABLE 5

Dissolution data for uncoated glipizide tablets prepared according to Example 3

| Time (hr) | % Active Released |
|---|---|
| 1.0 | 8.0 |
| 2.0 | 17.0 |
| 4.0 | 35.1 |
| 6.0 | 51.4 |
| 8.0 | 65.2 |
| 10.0 | 79.5 |
| 22.0 | 95.6 |

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. A composition comprising:
   (a) nanoparticles of spray-dried glipizide or a salt thereof, wherein the glipizide nanoparticles have an effective average particle size of less than 2000 nm; and
   (b) at least one surface stabilizer adsorbed on the surface of the glipizide nanoparticles;
   wherein:
   (i) the surface stabilizer is free of intermolecular cross-linkages;
   (ii) the glipizide nanoparticles or a salt thereof is present in an amount of from about 99.5% to about 0.001%, by weight, based on the total combined weight of the glipizide nanoparticles or a salt thereof and at least one surface stabilizer, not including other excipients;
   (iii) the at least one surface stabilizer is present in an amount of from about 0.5% to about 99.999% by weight, based on the total combined dry weight of the glipizide nanoparticles or a salt thereof and at least one surface stabilizer, not including other excipients;
   (iv) upon administration to a mammal, the glipizide nanoparticles redisperse such that the nanoparticles have an effective average particle size of less than 2 microns; and
   (v) the composition exhibits a $C_{max}$ which is at least 50% greater than the $C_{max}$ exhibited by a non-nanoparticulate glipizide composition when administered at the same dosage.

2. The composition of claim 1, wherein the glipizide is selected from the group consisting of a crystalline phase, an amorphous phase, and a semi-crystalline phase.

3. The composition of claim 1, wherein the effective average particle size of the spray-dried glipizide nanoparticles is selected from the group consisting of less than 1900 nm, less than 1800 nm, less than 1700 nm, less than 1600 nm, less than 1500 nm, less than 1400 nm, less than 1300 nm, less than 1200 nm, less than 1100 nm, less than 1000 nm, less than 900 nm, less than 800 nm, less than 700 nm, less than 600 nm, less than 500 nm, less than 400 nm, less than 300 nm, less than 250 nm, less than 200 nm, less than 100 nm, less than 75 nm, and less than 50 nm.

4. The composition of claim 1, wherein the composition is formulated for administration selected from the group consisting of oral, pulmonary, rectal, ophthalmic, colonic, parenteral, intracisternal, intravaginal, intraperitoneal, local, buccal, nasal, and topical administration.

5. The composition of claim 1 formulated into a dosage form selected from the group consisting of liquid dispersions, oral suspensions, gels, aerosols, ointments, creams, controlled release formulations, fast melt formulations, lyophilized formulations, tablets, capsules, delayed release formulations, extended release formulations, pulsatile release formulations, and mixed immediate release and controlled release formulations.

6. The composition of claim 1, wherein the composition further comprises one or more pharmaceutically acceptable excipients, carriers, or a combination thereof.

7. The composition of claim 1, comprising at least two surface stabilizers.

8. The composition of claim 1, wherein the surface stabilizer is selected from the group consisting of an anionic surface stabilizer, a cationic surface stabilizer, a zwitterionic surface stabilizer, and an ionic surface stabilizer.

9. The composition of claim 8, wherein the at least one surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hypromellose, carboxymethylcellulose sodium, methylcellulose, hydroxyethylcellulose, hypromellose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers; poloxamines, a charged phospholipid, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl-D-glucopyranoside; n-decyl-D-maltopyranoside; n-dodecyl-D-glucopyranoside; n-dodecyl-D-maltoside; heptanoyl-N-methylglucamide; n-heptyl-D-glucopyranoside; n-heptyl-D-thioglucoside; n-hexyl-D-glucopyranoside; nonanoyl-N-methylglucamide; n-noyl-D-glucopyranoside; octanoyl-N-methylglucamide; n-octyl-D-glucopyranoside; octyl-D-thioglucopyranoside; lysozyme, PEG-phospholipid, PEG-cholesterol, PEG-cholesterol derivative, PEG-vitamin A, and random copolymers of vinyl acetate and vinyl pyrrolidone.

10. The composition of claim 8, wherein the at least one cationic surface stabilizer is selected from the group consisting of a polymer, a biopolymer, a polysaccharide, a cellulosic, an alginate, a nonpolymeric compound, and a phospholipid.

11. The composition of claim 8, wherein the surface stabilizer is selected from the group consisting of cationic lipids, polymethylmethacrylate trimethylammonium bromide, sulfonium compounds, polyvinylpyrrolidone-2-dimethylaminoethyl methacrylate dimethyl sulfate, hexadecyltrimethyl ammonium bromide, phosphonium compounds, quarternary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$dimethyl hydroxyethyl ammonium chloride, $C_{12-15}$dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, alkyl pyridinium salts; amines, amine salts, amine oxides, imide azolinium salts, protonated quaternary acrylamides, methylated quaternary polymers, and cationic guar.

12. The composition of any of claim 8, 10, or 11, wherein the composition is bioadhesive.

13. The composition of claim 1, comprising as a surface stabilizer hydroxypropyl cellulose.

14. The composition of claim 1 further comprising at least one additional glipizide composition having an effective average particle size which is different from the effective average particle size of the spray-dried glipizide nanoparticles of (a).

15. The composition of claim 1, additionally comprising one or more non-glipizide active agents.

16. The composition of claim 15, wherein said additional one or more non-glipizide active agents are selected from the group consisting of nutraceuticals, amino acids, proteins, peptides, nucleotides, anti-obesity drugs, central nervous system stimulants, carotenoids, corticosteroids, elastase inhibitors, anti-fungals, oncology therapies, anti-emetics, analgesics, cardiovascular agents, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives, astringents, alpha-adrenergic receptor blocking agents, beta-adrenoceptor blocking agents, blood products, blood substitutes, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin, parathyroid biphosphonates, prostaglandins, radiopharmaceuticals, sex hormones, anti-allergic agents, stimulants, anoretics, sympathomimetics, thyroid agents, vasodilators, and xanthines.

17. The composition of claim 15, wherein said additional one or more non-glipizide active agents are selected from the group consisting of acyclovir, alprazolam, altretamine, amiloride, amiodarone, benztropine mesylate, bupropion, cabergoline, candesartan, cerivastatin, chlorpromazine, ciprofloxacin, cisapride, clarithromycin, clonidine, clopidogrel, cyclobenzaprine, cyproheptadine, delavirdine, desmopressin, diltiazem, dipyridamole, dolasetron, enalapril maleate, enalaprilat, famotidine, felodipine, furazolidone, glipizide, irbesartan, ketoconazole, lansoprazole, loratadine, loxapine, mebendazole, mercaptopurine, milrinone lactate, minocycline, mitoxantrone, nelfinavir mesylate, nimodipine, norfloxacin, olanzapine, omeprazole, penciclovir, pimozide, tacolimus, quazepam, raloxifene, rifabutin, rifampin, risperidone, rizatriptan, saquinavir, sertraline, sildenafil, acetylsulfisoxazole, temazepam, thiabendazole, thioguanine, trandolapril, triamterene, trimetrexate, troglitazone, trovafloxacin, verapamil, vinblastine sulfate, mycophenolate, atovaquone, atovaquone, proguanil, ceftazidime, cefuroxime, etoposide, terbinafine, thalidomide, fluconazole, amsacrine, dacarbazine, teniposide, and acetylsalicylate.

18. The composition of claim 1, wherein upon administration the composition redisperses such that the spray-dried glipizide nanoparticles have an effective average particle size selected from the group consisting of less than 1900 nm, less than 1800 nm, less than 1700 nm, less than 1600 nm, less than 1500 nm, less than 1400 nm, less than 1300 nm, less than 1200 nm, less than 1100 nm, less than 1000 nm, less than 900 nm, less than 800 nm, less than 700 nm, less than 600 nm, less than 500 nm, less than 400 nm, less than 300 nm, less than 250 nm, less than 200 nm, less than 150 nm, less than 100 nm, less than 75 nm, and less than 50 nm.

19. The composition of claim 1, wherein the composition redisperses in a biorelevant media such that the spray-dried nanoparticles have an effective average particle size of less than 2 microns.

20. The composition of claim 19, wherein the biorelevant media is selected from the group consisting of water, aqueous electrolyte solutions, aqueous solutions of a salt, aqueous solutions of an acid, aqueous solutions of a base, and combinations thereof.

21. The composition of claim 19, wherein the composition redisperses in a biorelevant media such that the spray-dried glipizide nanoparticles have an effective average particle size selected from the group consisting of less than 1900 nm, less than 1800 nm, less than 1700 nm, less than 1600 nm, less than 1500 nm, less than 1400 nm, less than 1300 nm, less than 1200 nm, less than 1100 nm, less than 1000 nm, less than 900 nm, less than 800 nm, less than 700 nm, less than 600 nm, less than 500 nm, less than 400 nm, less than 300 nm, less than 250 nm, less than 200 nm, less than 150 nm, less than 100 nm, less than 75 nm, and less than 50 nm.

22. The composition of claim 1 formulated into a liquid dosage form, wherein the dosage form has a viscosity of less than 2000 mPa·s, measured at 20° C., at a shear rate of 0.1 (1/s).

23. The composition of claim 22, having a viscosity at a shear rate of 0.1 (1/s), measured at 20° C., selected from the group consisting of from about 2000 mPa·s to about 1 mPa·s, from about 1900 mPa·s to about 1 mPa·s, from about 1800 mPa·s to about 1 mPa·s, from about 1700 mPa·s to about 1 mPa·s, from about 1600 mPa·s to about 1 mPa·s, from about 1500 mPa·s to about 1 mPa·s, from about 1400 mPa·s to about 1 mPa·s, from about 1300 mPa·s to about 1 mPa·s, from about 1200 mPa·s to about 1 mPa·s, from about 1100 mPa·s to about 1 mPa·s, from about 1000 mPa·s to about 1 mPa·s, from about 900 mPa·s to about 1 mPa·s, from about 800 mPa·s to about 1 mPa·s, from about 700 mPa·s to about 1 mPa·s, from about 600 mPa·s to about 1 mPa·s, from about 500 mPa·s to about 1 mPa·s, from about 400 mPa·s to about 1 mPa·s, from about 300 mPa·s to about 1 mPa·s, from about 200 mPa·s to about 1 mPa·s, from about 175 mPa·s to about 1 mPa·s, from about 150 mPa·s to about 1 mPa·s, from about 125 mPa·s to about 1 mPa·s, from about 100 mPa·s to about 1 mPa·s, from about 75 mPa·s to about 1 mPa·s, from about 50 mPa·s to about 1 mPa·s, from about 25 mPa·s to about 1 mPa·s, from about 15 mPa·s to about 1 mPa·s, from about 10 mPa·s to about 1 mPa·s, and from about 5 mPa·s to about 1 mPa·s.

24. The composition of claim 22, wherein the viscosity of the dosage form is selected from the group consisting of less than 1/200, less than 1/100, less than 1/50, less than 1/25, and less than 1/10 of the viscosity of a liquid dosage form of a non-nanoparticulate composition of glipizide, at about the same concentration per ml of glipizide.

25. The composition of claim 22, wherein the viscosity of the dosage form is selected from the group consisting of less than 5%, less than 10%, less than 15%, less than 20%, less than 25%, less than 30%, less than 35%, less than 40%, less than 45%, less than 50%, less than 55%, less than 60%, less than 65%, less than 70%, less than 75%, less than 80%, less than 85%, and less than 90% of the viscosity of a liquid dosage form of a non-nanoparticulate composition of the glipizide, at about the same concentration per ml of glipizide.

26. A method of treating diabetes in a subject in need thereof comprising administering to the subject an effective amount of a composition comprising:
(a) nanoparticles of a spray-dried glipizide or a salt thereof, wherein the glipizide nanoparticles have an effective average particle size of less than 2000 nm; and
(b) at least one surface stabilizer adsorbed on the surface of the glipizide nanoparticles,
wherein:
(i) the surface stabilizer is free of intermolecular cross-linkages;
(ii) the nanoparticle glipizide or a salt thereof is present in an amount of from about 99.5% to about 0.001%, by weight, based on the total combined weight of the nanoparticle glipizide or a salt thereof and at least one surface stabilizer, not including other excipients;
(iii) the at least one surface stabilizer is present in an amount of from about 0.5% to about 99.999% by weight, based on the total combined dry weight of the nanoparticle glipizide or a salt thereof and at least one surface stabilizer, not including other excipients;
(iv) upon administration to a mammal, the glipizide nanoparticles redisperse such that the nanoparticles have an effective average particle size of less than 2 microns; and
(v) the composition exhibits a $C_{max}$ which is at least 50% greater than the $C_{max}$ exhibited by a non-nanoparticulate glipizide composition when administered at the same dosage.

27. The method of claim 26, wherein the glipizide or a salt thereof is selected from the group consisting of a crystalline phase, an amorphous phase, and a semi-crystalline phase.

28. The method of claim 26, wherein the effective average particle size of the spray-dried glipizide nanoparticles is selected from the group consisting of less than 1900 nm, less than 1800 nm, less than 1700 nm, less than 1600 nm, less than 1500 nm, less than 1400 nm, less than 1300 nm, less than 1200 nm, less than 1100 nm, less than 1000 nm, less than 900 nm, less than 800 nm, less than 700 nm, less than 600 nm, less than 500 nm, less than 400 nm, less than 300 nm, less than 250 nm, less than 200 nm, less than 100 nm, less than 75 nm, and less than 50 nm.

29. The method of claim 26, wherein the composition is formulated for administration selected from the group consisting of oral, pulmonary, rectal, ophthalmic, colonic, parenteral, intracisternal, intravaginal, intraperitoneal, local, buccal, nasal, and topical administration.

30. The method of claim 26, wherein the composition is a dosage form selected from the group consisting of liquid dispersions, oral suspensions, gels, aerosols, ointments, creams, controlled release formulations, fast melt formulations, lyophilized formulations, tablets, capsules, delayed release formulations, extended release formulations, pulsatile release formulations, and mixed immediate release and controlled release formulations.

31. The method of claim 26, wherein the composition further comprises one or more pharmaceutically acceptable excipients, carriers, or a combination thereof.

32. The method of claim 26, utilizing at least two surface stabilizers.

33. The method of claim 26, wherein the surface stabilizer is selected from the group consisting of an anionic surface stabilizer, a cationic surface stabilizer, a zwitterionic surface stabilizer, and an ionic surface stabilizer.

34. The method of claim 33, wherein the at least one surface stabilizer is selected from the group consisting of cetyl pyridinium chloride, gelatin, casein, phosphatides, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hypromellose, carboxymethylcellulose sodium, methylcellulose, hydroxyethylcellulose, hypromellose phthalate, noncrystalline cellulose, magnesium aluminum silicate, triethanolamine, polyvinyl alcohol, polyvinylpyrrolidone, 4-(1,1,3,3-tetramethylbutyl)-phenol polymer with ethylene oxide and formaldehyde, poloxamers; poloxamines, a charged phospholipid, dioctylsulfosuccinate, dialkylesters of sodium sulfosuccinic acid, sodium lauryl sulfate, alkyl aryl polyether sulfonates, mixtures of sucrose stearate and sucrose distearate, p-isononylphenoxypoly-(glycidol), decanoyl-N-methylglucamide; n-decyl-D-glucopyranoside; n-decyl-D-maltopyranoside; n-dodecyl-D-glucopyranoside; n-dodecyl-D-maltoside; heptanoyl-N-methylglucamide; n-heptyl-D-glucopyranoside; n-heptyl-D-thioglucoside; n-hexyl-D-glucopyranoside; nonanoyl-N-methylglucamide; n-noyl-D-glucopyranoside; octanoyl-N-methylglucamide; n-octyl-D-glucopyranoside; octyl-D-thioglucopyranoside; lysozyme, PEG-phospholipid, PEG-cholesterol, PEG-cholesterol derivative, PEG-vitamin A, PEG-vitamin E, and random copolymers of vinyl acetate and vinyl pyrrolidone.

35. The method of claim 33, wherein the at least one cationic surface stabilizer is selected from the group consisting of a polymer, a biopolymer, a polysaccharide, a cellulosic, an alginate, a nonpolymeric compound, and a phospholipid.

36. The method of claim 33, wherein the surface stabilizer is selected from the group consisting of benzalkonium chloride, polymethylmethacrylate trimethylammonium bromide, polyvinylpyrrolidone-2-dimethylaminoethyl methacrylate dimethyl sulfate, hexadecyltrimethyl ammonium bromide, cationic lipids, sulfonium compounds, phosphonium compounds, quaternary ammonium compounds, benzyl-di(2-chloroethyl)ethylammonium bromide, coconut trimethyl ammonium chloride, coconut trimethyl ammonium bromide, coconut methyl dihydroxyethyl ammonium chloride, coconut methyl dihydroxyethyl ammonium bromide, decyl triethyl ammonium chloride, decyl dimethyl hydroxyethyl ammonium chloride, decyl dimethyl hydroxyethyl ammonium chloride bromide, $C_{12-15}$ dimethyl hydroxyethyl ammonium chloride, $C_{12-15}$ dimethyl hydroxyethyl ammonium chloride bromide, coconut dimethyl hydroxyethyl ammonium chloride, coconut dimethyl hydroxyethyl ammonium bromide, myristyl trimethyl ammonium methyl sulphate, lauryl dimethyl benzyl ammonium chloride, lauryl dimethyl benzyl ammonium bromide, lauryl dimethyl (ethenoxy)$_4$ ammonium chloride, lauryl dimethyl (ethenoxy)$_4$ ammonium bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts, dialkyl-dimethylammonium salts, lauryl trimethyl ammonium chloride, ethoxylated alkyamidoalkyldialkylammonium salt, an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride, dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$ trimethyl ammonium bromides, $C_{15}$ trimethyl ammonium bromides, $C_{17}$ trimethyl ammonium bromides, dodecylbenzyl triethyl ammonium chloride, poly-diallyldimethylammonium chloride dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride, tetrabutylammonium bromide, benzyl trimethylammonium bromide, choline esters, benzalkonium chloride, stearalkonium chloride compounds, cetyl pyridinium bromide, cetyl pyridinium chloride, halide salts of quaternized polyoxyethylalkylamines, alkyl pyridinium salts; amines, amine salts, amine oxides, imide azolinium salts, protonated quaternary acrylamides, methylated quaternary polymers, and cationic guar.

37. The method of any of claim 33, 35, or 36, wherein the composition is bioadhesive.

38. The method of claim 26, utilizing hydroxypropylcellulose as a surface stabilizer.

39. The method of claim 26, additionally comprising administering one or more non-glipizide active agents.

40. The method of claim 39, wherein said additional one or more non-glipizide active agents are selected from the group consisting of nutraceuticals, amino acids, proteins, peptides, nucleotides, anti-obesity drugs, central nervous system stimulants, carotenoids, corticosteroids, elastase inhibitors, anti-fungals, oncology therapies, anti-emetics, analgesics, cardiovascular agents, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives, astringents, alpha-adrenergic receptor blocking agents, beta-adrenoceptor blocking agents, blood products, blood substitutes, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin, parathyroid biphosphonates, prostaglandins, radio-pharmaceuticals, sex hormones, anti-allergic agents, stimulants, anoretics, sympathomimetics, thyroid agents, vasodilators, and xanthines.

41. The method of claim 39, wherein said additional one or more non-glipizide active agents are selected from the group consisting of acyclovir, alprazolam, altretamine, amiloride, amiodarone, benztropine mesylate, bupropion, cabergoline, candesartan, cerivastatin, chlorpromazine, ciprofloxacin, cisapride, clarithromycin, clonidine, clopidogrel, cyclobenzaprine, cyproheptadine, delavirdine, desmopressin, diltiazem, dipyridamole, dolasetron, enalapril maleate, enalaprilat, famotidine, felodipine, furazolidone, glipizide, irbesartan, ketoconazole, lansoprazole, loratadine, loxapine, mebendazole, mercaptopurine, milrinone lactate, minocycline, mitoxantrone, nelfinavir mesylate, nimodipine, norfloxacin, olanzapine, omeprazole, penciclovir, pimozide, tacolimus, quazepam, raloxifene, rifabutin, rifampin, risperidone, rizatriptan, saquinavir, sertraline, sildenafil, acetylsulfisoxazole, temazepam, thiabendazole, thioguanine, trandolapril, triamterene, trimetrexate, troglitazone, trovafloxacin, verapamil, vinblastine sulfate, mycophenolate, atovaquone, atovaquone, proguanil, ceftazidime, cefuroxime, etoposide, terbinafine, thalidomide, fluconazole, amsacrine, dacarbazine, teniposide, and acetylsalicylate.

42. The method of claim 26, wherein the subject is a human.

43. The method of claim 26, wherein the method is used to treat indications where blood-glucose lowering drugs are typically used.

44. The method of claim 26, wherein the method is used to treat diabetes.

45. The method of claim 44, wherein the diabetes is non-insulin dependent diabetes mellitus.

46. The composition of claim 1, wherein:
(i) the surface stabilizer is hydroxypropyl cellulose; and
(ii) the composition is formulated into a fast melt formulation, which disintegrates in less than 1 minute upon contact with water.

47. The composition of claim 1, wherein:
(i) the surface stabilizer is hydroxypropyl cellulose; and
(ii) the composition is formulated into a controlled release formulation.

48. The composition of claim 47, wherein the controlled release formulation of the composition has a steady release over a time period of about 16 hours.

49. The composition of claim 47, wherein the controlled release formulation of the composition is uncoated and has a steady release over a time period of about 22 hours.

* * * * *